United States Patent

Oishi et al.

[11] Patent Number: 6,008,188
[45] Date of Patent: Dec. 28, 1999

[54] CYTOKINE POTENTIATOR AND PHARMACEUTICAL FORMULATION FOR CYTOKINE ADMINISTRATION

[75] Inventors: Yuichi Oishi; Masaki Yoshida; Shintaro Inoue, all of Odawara, Japan

[73] Assignee: Kanebo Limited, Japan

[21] Appl. No.: 08/737,064

[22] PCT Filed: Apr. 28, 1995

[86] PCT No.: PCT/JP95/00857

§ 371 Date: Dec. 16, 1996

§ 102(e) Date: Dec. 16, 1996

[87] PCT Pub. No.: WO95/30412

PCT Pub. Date: Nov. 16, 1995

[30] Foreign Application Priority Data

May 6, 1994 [JP] Japan .................................. 6-117495

[51] Int. Cl.⁶ ............................ A01N 37/18; A01N 37/12
[52] U.S. Cl. ............................ 514/2; 514/561; 514/667; 514/669; 514/673; 562/567; 564/503; 424/85.1; 424/85.2; 424/85.4
[58] Field of Search ............................ 514/2, 561, 673, 514/669, 667; 564/503; 562/567; 424/85.1, 85.2, 85.4

[56] References Cited

U.S. PATENT DOCUMENTS

| | | | |
|---|---|---|---|
| 4,423,223 | 12/1983 | Huggins et al. | 424/181 |
| 4,469,684 | 9/1984 | Hall et al. | 548/163 |
| 5,189,166 | 2/1993 | Hull | 544/298 |
| 5,332,758 | 7/1994 | Nakata et al. | 514/561 |
| 5,543,394 | 8/1996 | Wozney et al. | 514/12 |
| 5,591,709 | 1/1997 | Lindenbaum | 514/4 |

FOREIGN PATENT DOCUMENTS 229016  7/1987  European Pat. Off. ....... A61K 37/02

OTHER PUBLICATIONS

Zhang et al., Immunology, vol. 79:528–534, Dec., 1993.
Zwierzina et al., Stem Cells, vol. 11:144–153, Nov. 1993.

*Primary Examiner*—Christina Y. Chan
*Assistant Examiner*—Patrick Nolan
*Attorney, Agent, or Firm*—Morrison Law Firm

[57] ABSTRACT

A cytokine activity enhancer comprising an ethanolamine derivative of the following general formula (I) or a salt thereof, or comprising it along with cytokine or a cytokine production promoter; and also a medicine for diseases with lowered cytokine activity, comprising, as the active ingredient, the cytokine activity enhancer:

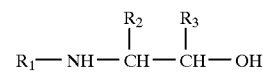

(I)

wherein $R_1$ is H, $-CH_3$, $-CH_2CH(CH_3)OH$ or $-CH_2CH_2OH$; $R_2$ is H, $-CH_3$, $-CH_2CH_3$ or $-COOH$; and $R_3$ is H, $-CH_3$, $-CH_2CH_3$ or $-CH_2NH_2$.

2 Claims, 1 Drawing Sheet

CYTOKINE POTENTIATOR AND PHARMACEUTICAL FORMULATION FOR CYTOKINE ADMINISTRATION

TECHNICAL FIELD

The present invention relates to a cytokine potentiator and a medicine for diseases with lowered cytokine activity. In particular, the present invention relates to a cytokine activity enhancer and a medicine for diseases associated with lowered cytokine activity, which can enhance the cellular response to cytokines. The present invention enhances the reactivity of cytokines lowered by aging or the like, and can treat disorders caused by a decrease in cytokine activity.

BACKGROUND OF THE INVENTION

It is known that the restoration of aged skin tissue or chapped skin tissue to its original condition is closely associated with cytokine activity. In addition, it is known that changes in cytokine activities are closely correlated with certain diseases. Various attempts to use cytokines to treat these diseases have been and are being actively pursued.

Cytokines may be administered to patients orally or by parenteral administration, such as by injection or endermic application. However, these methods require continuous administration of a large amount of expensive cytokines to the patient until complete recovery is achieved. These methods are therefore costly and time-consuming.

Alternatively, a substance that promotes the production of cytokines may be administered. Like direct administration of cytokines, the substance may be administered to the patient orally or by parenteral administration such as injection or endermic application. However, like the administration of cytokines, the administration of cytokine production enhancers are costly and time-consuming.

The administration of large amounts of cytokines for extended periods of time is further problematic in that the treatment often disrupts the patient's overall metabolism. In addition, external application of cytokines are ineffective in achieving a local effect, due to decomposition or poor absorbability of the compound. Therefore, a safer method for treating aged or chapped skin is desirable.

OBJECTS AND SUMMARY OF THE INVENTION

For the purposes of this specification, cytokine potentiator is defined as a substance which augments the efficacy of a cytokine, accelerates the activity of a cytokine, acts as a carrier for a cytokine, increases a cytokine's affinity or avidity for its receptor, improves the cellular response to a cytokine in vivo or in vitro, acts in the manner of an adjuvant, directs the localization of a cytokine, or in any manner improves the way in which a cytokine exerts its function on the target.

Accordingly, an object of the present invention is to provide a cytokine activity enhancer or a medicine for treating diseases characterized by lowered cytokine activity which, when administered to an individual, can increase cellular response to endogenous cytokines.

Another object of the present invention is to provide a cytokine activity enhancer or a medicine for treating diseases characterized by lowered cytokine activity which, when administered along with exogenous cytokines, can reduce the amount of cytokines to be administered.

The present invention provides a cytokine activity enhancer comprising an ethanolamine derivative of the following general formula (I) or a salt thereof.

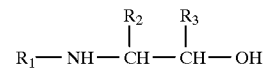

wherein $R_1$ represents H, —$CH_3$, —$CH_2CH(CH_3)OH$ or —$CH_2CH_2OH$; $R_2$ represents H, —$CH_3$, —$CH_2CH_3$ or —COOH; and $R_3$ represents H, —$CH_3$, —$CH_2CH_3$ or —$CH_2NH_2$.

The present invention also provides a medicine to treat diseases characterized by lowered cytokine activities, which comprises the above-mentioned cytokine activity enhancer.

BEST MODES OF CARRYING OUT THE INVENTION

Figure 1:
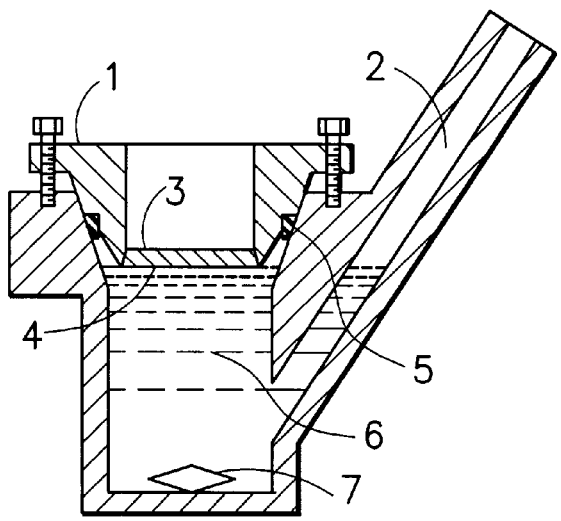
FIG. 1 shows a vertical diffusion cell device used in Test Example 15.

Of the ethanolamine derivatives of formula (I) intended for use in the present invention, the preferred forms are those wherein $R_1$ is H, $R_2$ is H, —$CH_3$ or —$CH_2CH_3$, and $R_3$ is H, —$CH_3$, —$CH_2CH_3$ or —$CH_2NH_2$, and those where $R_1$ is —$CH_3$, $R_2$ is —COOH, and $R_3$ is H, —$CH_3$, —$CH_2CH_3$ or —$CH_2NH_2$. Also preferred are those where $R_1$ is —$CH_3$, —$CH_2CH(CH_3)OH$ or —$CH_2CH_2OH$, $R_2$ is H, and $R_3$ is H, —$CH_3$, —$CH_2CH_3$ or —$CH_2NH_2$.

Specific examples of the preferred ethanolamine derivatives of formula (I) are N-methyl-L-serine, diethanolamine, ethanolamine, N-methylethanolamine, diisopropanolamine, D,L-2-amino-1-propanol, 2-amino-1-butanol, 1,3-diamino-2-propanol, 1-amino-2-butanol, and the like.

Salts of ethanolamine derivatives of formula (I) are not specifically defined, but include such pharmaceutically-acceptable salts as inorganic acid salts, such as hydrochlorides, hydrobromides, sulfates, phosphates, and the like, as well as organic acid salts, such as acetates, fumarates, maleates, tartrates, citrates, p-toluenesulfonates, and the like.

Cytokines as referred to herein include platelet-derived growth factor (hereinafter referred to as PDGF), fibroblast growth factor (hereinafter referred to as FGF), epidermal growth factor (hereinafter referred to as EGF), transforming growth factor (hereinafter referred to as TGF), bone morphogenetic protein (hereinafter referred to as BMP), interferon (hereinafter referred to as IFN), granulocyte colony-stimulating factor (hereinafter referred to as G-CSF), macrophage colony-stimulating factor (hereinafter referred to as M-CSF), insulin-like growth factor (hereinafter referred to as IGF), hepatocyte growth factor (hereinafter referred to as HGF), stem cell factor (hereinafter referred to as SCF), nerve growth factor (hereinafter referred to as NGF), vascular endothelial cell growth factor (hereinafter referred to as VEGF), keratinocyte growth factor (hereinafter referred to as KGF), interleukin (see Interleukin Network, Kodan-sha, 1992, the entirety of which is herein incorporated by reference), and the like. Of these cytokines, those which activate tyrosine or serine/threonine kinases, and also activate the phosphorylation of tyrosine, or serine and/or threonine residues on subunits of tyrosine or serine/threonine kinase-linked receptors, respectively, are preferred effectors.

Cytokines which activate tyrosine or serine/threonine kinases and which also activate the phosphorylation of tyrosine or serine and/or threonine residue on the subunits of tyrosine or serine/threonine kinase-linked receptors, respectively, include EGF, IGF, FGF, PDGF, M-CSF, SCF, VEGF, NGF, HGF, IL 2 and TGF.

The use of cytokines to treat diseases include the use of basic FGF (hereinafter referred to as βFGF), EGF (see Modern Chemistry, extra number 16, Tokyo Kagaku Dojin-sha, p. 131, herein incorporated by reference), PDGF (Gendai Kagaku, extra number 4, Tokyo Kagaku Dojin-sha, p. 114, 1985, herein incorporated by reference), TGF alpha (TGF-α) that bonds to EGF receptors (see Cytokine, Medical View Co., p. 10, 1991, herein incorporated by reference) and acidic FGF (see Molecular Medicine, Vol. 30, p. 1993, herein incorporated by reference) to treat cerebral paralysis, pressure sores, wounds and ulcers. Cytokines have been used as anti-ulcerous agents to treat gastric ulcers, and in the treatment of myocardial infarction. The use of BMP to treat osteoporosis is expected to increase with the increase in aged populations (see Experimental Medicine, Vol. 10, No. 15, p. 2010, 1992, herein incorporated by reference).

TGF beta 1 (hereinafter referred to as TGF-β1) has been studied as an agent to enhance healing of bone fractures. In addition, TGF-β1 has also been studied as an agent for the treatment of rheumatism, due to its ability to inhibit the production of some matrix metalloproteases, and its ability to promote the production of tissue inhibitor of metalloproteases (hereinafter referred to as TIMP) (see Experimental Medicine, Vol. 10, No. 15, p. 1860, 1992, herein incorporated by reference). In addition, TGF-β1 has also been studied as an agent to promote wound healing, due to its ability to promote the synthesis of type I collagen.

Hepatocyte growth factor (hereinafter referred to as HGF) has activity as an organ-regenerating agent, and therefore may be useful in organ transplants, a procedure that is becoming increasingly popular. HGF also may be useful to treat cancer, since it has shown some activity in inhibiting the propagation of tumor cells (see FEBS Letters, Vol. 2, p. 229, 1991, herein incorporated by reference).

IFN-gamma (IFNγ) and G-CSF are also used to treat cancer, due to their ability to enhance immune system responses.

Interleukin-2 (IL-2) has been used to treat malignant hemangiocytoma. In addition, IL-2 is used for LAK (lymphocyte-activated killer cell) therapy to combat cancer. LAK therapy is an immunological enhancement therapy in which lymphocytes of a patient are incubated in vitro, in the presence of added IL-2, to increase the number of cytopathic T-lymphocytes (CTLs) and natural killer cells (NK cells). The thus-incubated lymphocytes are returned to the patient. (see Hiroshi Kobayashi, "Curing of Cancer", published by Iwanami Shin-sho, 292, pp. 151–154, 1993, herein incorporated by reference).

Interleukin-12 (IL-12) is known to act in a manner similar to IL-2; however, IL-12 but has a higher activity than IL-2 (see Experimental Medicine, Vol. 10, No. 3, pp. 395–399, 1992, herein incorporated by reference). IL-12 has also been studied for use as a carcinostatic agent, and for use in LAK therapy (see Nikkei Biotechnology, No. 277, pp. 2–3, 1993, herein incorporated by reference).

For a current example of therapeutic use of cytokines in the treatment of AIDS, see: Sneller, M. C., Cytokine therapy of HIV infection, Adv Exp Med Biol 394:411–419, 1996 the entirety of which is incorporated herein by reference.

For a current example of therapeutic use of cytokines in the treatment of multiple sclerosis, see: Kelley, C. L., The role of interferons in the treatment of multiple sclerosis, J Neurosci Nurs 28(2):114–120, 1996, the entirety of which is incorporated herein by reference.

For a current example of therapeutic use of cytokines in the treatment of hematologic diseases, see: Waage, A., Dahl, I. M., Evensen, S. A., Holte, H., Lamvik, J., Sletnes, K., Wisloff, F., Treatment with growth factors and cytokines in hematologic diseases, Tidsskr Nor Laegeforen 116(12):1465–1469, 1996, the entirety of which is incorporated herein by reference.

For a current example of therapeutic use of cytokines in the treatment of mast-cell-mediated skin diseases, see: Luger, T. A., Cytokine treatment of mast-cell-mediated skin diseases, Exp Dermatol 4(4.2):277–280, 1995, the entirety of which is incorporated herein by reference.

For a current example of therapeutic use of cytokines in the treatment of blood diseases, see: Robak, T., Cytokines in the treatment of blood diseases, Acta Haematol Pol 26(2) (Suppl 1):72–78, 1995, the entirety of which is incorporated herein by reference.

For a current example of therapeutic use of cytokines in gene therapy, see: Schmidt-Wolf, G. D.; Schmidt-Wolf, I. G., Cytokines and gene therapy, Immunol Today 16(4):173–175, 1995, the entirety of which is incorporated herein by reference.

For a current example of therapeutic use of cytokines in the treatment of leishmania, see: Ho, J. L.; Badaro, R.; Hatzigeorgiou, D.; Reed, S. G.; Johnson, W. D. Jr., Cytokines in the treatment of leishmaniasis: from studies of immunopathology to patient therapy, Biotherapy 7(3-4):223–235, 1994, the entirety of which is incorporated herein by reference.

For a current example of therapeutic use of cytokines in the treatment of fungal infections, see: Kullberg, B. J.; van't Wout, J. W., Cytokines in the treatment of fungal infections, Biotherapy 7(3-4):195–210, 1994, the entirety of which is incorporated herein by reference.

For a current example of therapeutic use of cytokines in the treatment of legionella, see: Byrd, T. F., Cytokines and legionellosis, Biotherapy 7(3-4):179–186, 1994, the entirety of which is incorporated herein by reference.

For a current example of therapeutic use of cytokines in the treatment of inflammatory rheumatic diseases, see: Kalden, J. R., Biologic agents in the therapy of inflammatory rheumatic diseases, including therapeutic antibodies, cytokines, and cytokine antagonists, Curr Opin Rheumatol 6(3):281–286, 1994, the entirety of which is incorporated herein by reference.

For a current example of therapeutic use of cytokines in the treatment of tuberculosis, see: Wallis, R. S.; Ellner, J. J., Cytokines and tuberculosis, J Leukoc Biol 55(5):686–681, 1994, the entirety of which is incorporated herein by reference.

For a current example of therapeutic use of cytokines in the treatment of alcoholic liver disease, see: McClain, C.; Hill, D.; Schmidt, J.; Diehl, A. M., Cytokines and alcoholic liver disease, Semin Liver Dis 13(2):170–182, 1993, the entirety of which is incorporated herein by reference.

For a current example of therapeutic use of cytokines in the treatment of myelodysplastic syndromes, see: Ganser, A.; Seipelt, G.; Eder, M.; Geissler, G.; Ottmann, O. G.; Hess, U.; Hoelzer, D., Treatment of myelodysplastic syndromes with cytokines and cytotoxic drugs, Semin Oncol 19(2) (suppl):95–101, 1992, the entirety of which is incorporated herein by reference.

For a current examples and reviews of the therapeutic use of cytokines in the treatment of cancers, see:—Geller, R. B., Use of cytokines in the treatment of acute myelocytic leukemia: a critical review, J Clin Oncol 14(4):1371–1382, 1996;—Jako, J.; Arato, G.; Domjan, G.; Hasitz, A.; Hollo, G.; Peto, M.; Stelich, G.; Schopper, J., Cytokines in the treatment of malignancies, Acta Med Hung 50(3-4):257–273, 1994;—Mizuno, M.; Yoshida, J., Cytokine gene therapy for malignant brain tumors, Tanpakushitsu Kakusan Koso 40(17): 2709–2712, 1995;—Hanada, K.; Hamada, H., Immunogene therapy of cancer using cytokine genes, Tanpakushitsu Kakusan Koso 40(17):2688–2693, 1995;—Hamasaki, V. K.; Vokes, E. E., Interferons and other cytokines in head and neck cancer, Med Oncol 12(1):23–33, 1995;—Tomao, S.; Mozzicafreddo, A.; Raffaele, M.; Romiti, A.; Papo, M. A.; Campisi, C., Interferons in the therapy of solid tumors, Clin Ter 146(8-9):491–502, 1995;—Triebel, F.; Escudier, B., Cytokines and solid tumors, Rev Prat 43(5):580–585, 1993;—Ebert, T.; Schmitz-Drager, B. J.; Ackermann, R., The role of cytokines in the therapy of renal cell carcinoma, Recent Results Cancer Res 126:113–118, 1993;—Schuler, M.; Huber, C.; Peschel, C., Cytokines in the pathophysiology and treatment of chronic B-cell malignancies: A review, Ann Hematol 71(2):57–63, 1995;—Otto, T.; Goepel, M.; Luboldt, H. J.; Rubben, H., Cytokine therapy of metastatic renal cell carcinoma, Urologe A 34(3):200–203, 1995;—Garbe, C., Perspectives of cytokine treatment in malignant skin tumors, Recent Results Cancer Res 139:349–369, 1995;—Balkwill, F. R., Cytokine therapy of cancer. The importance of knowing the context, Eur Cytokine Netw 5(4):379–385, 1994;—Okada, H.; Okamoto, S.; Yoshida, J., Gene therapy for brain tumors: cytokine gene therapy using DNA/liposome (series 3), No Shinkei Geka 22(11):999–1004, 1994;—Buer, J.; Kirchner, H.; Schomburg, A.; Schuler, A.; Manns, M.; Lopez-Hanninen, E.; Duensing, S.; Poliwoda, H.; Atzpodien, J., Cytokine-based biotherapy of gastrointestinal tumors, Clin Investig 72(7):526–534, 1994;—Foa, R.; Cignetti, A.; Riera, L.; Gillio Tos, A.; Guarini, A., Cytokine gene therapy in oncology, Folia Biol (Praha) 40(1-2):37–48, 1994;—Di Pierro, F.; Cavallo, F.; Pericle, F.; Bertini, S.; Giovarelli, M.; Forni, G., Strategies for cytokine utilisation in tumor therapy, Med Oncol Tumor Pharmacother 10(1-2):53–59, 1993;—Neidhart, J. A., Hematopoietic cytokines: Current use in cancer therapy, Cancer 72(11) (suppl):3381–3386, 1993;—Watanabe, N., Clinical application of anticancer cytokines, Nippon Rinsho 50(8):1973–1977, 1992;—Khan, I. U.; Shear, N. H., Cytokines in anticancer therapy, Clin Dermatol 9(4):523–533, 1991;—Oettgen, H. F., Cytokines in clinical cancer therapy, Curr Opin Immunol 3(5):699–705, 1991;—Cicco, N. A.; Lubbert, M.; Oster, W.; Lindemann, A.; Mertelsmann, R., Cytokines in the pathogenesis and management of non-Hodgkin's lymphomas, Hematol Oncol Clin North Am 5(5):1053–1066, 1991;—Atzpodien, J.; Kirchner, H., Cancer, cytokines, and cytotoxic cells: interleukin-2 in the immunotherapy of human neoplasms, Klin Wochenschr 68(1):1–11, 1990;—Borden, E. C.; Sondel, P. M., Lymphokines and cytokines as cancer treatment. Immunotherapy realized, Cancer 65(3) (Suppl):800–814, 1990;—Wagstaff, J.; Melief, K. J., Lymphokines and cytokines, Cancer Chemother Biol Response Modif 9:432–453, 1987;—Parkinson, D. R., Cytokines in cancer therapy, Urology 34(4) (Suppl):69–74, 1989;—Lindemann, A.; Oster, W.; Herrmann, F.; Mertelsmann, R., Cytokines in tumor therapy, Arzneimittelforschung 38(3A):466–469, 1988;—Ishida, N.; Yoshida, T., The role of cytokines in cancer therapy, Gan To Kagaku Ryoho 14(5)(Pt 1):1187–1193, 1987, each the entirety of which is incorporated herein by reference.

For a current review of therapeutic use of cytokines, see:—Tsudo, M., Cytokine and disease, Rinsho Byori 42(8):821–824, 1994;—Maruna, P.; Masek, Z., Cytokine therapy, Cas Lek Cesk 134(2):44–48, 1995;—Peschel, C.; Huber, C.; Aulitzky, W. E., Clinical applications of cytokines, Presse Med 23(23):1083–1091, 1994;—Wardle, E. N., Cytokines: an overview, Eur J Med 2(7):417–423, 1993;—Kliche, K. O.; Schneider, W., Therapeutic use of cytokines, Versicherungsmedizin 45(4):122–125, 1993;—Aulitzky, W. E.; Huber, C.; Peschel, C., Cytokine therapy of neoplastic and inflammatory disease, Int Arch Allergy Immunol 101(3):221–226, 1993;—Viadro, M. M., Cytokines and their role in the pathogenesis and therapy of infections, Antibiot Khimioter 35(9):12–14, 1990;—De Benedetti, F.; Marseglia, G. L.; Martini, A.; Burgio, G. R., Cytokines: present and future therapeutic applications, G Ital Chemioter 36(1-3):17–27, 1989, each the entirety of which is incorporated herein by reference.

For current reviews of therapeutic use of cytokines in the treatment of infectious diseases, see:—Lau, A. S., Cytokines in the pathogenesis and treatment of infectious diseases, Adv Pediatr Infect Dis 9:211–236, 1994;—Finter, N. B., Cytokines in the treatment of virus infections, Biotherapy 7(3-4):151–159, 1994; and—Beaman, M. H., Cytokine therapy of infectious diseases, Curr Clin Top Infect Dis 14:228–251, 1994, each the entirety of which is incorporated herein by reference.

The cytokine production promoter of the present invention includes, for example, a preparation (designated OK-432) comprising penicillin-killed *Streptococcus pyogenes,* glycyrrhizic acid, and glycyrrhetinic acid. OK-432 is used to treat cancer, and it has been confirmed that OK-432 produces IFN in the spleen cells of mice to which OK-432 is intraabdominally administered. Glychrrhizic acid, by itself, is used to treat hepatitis, and also has an IFN-producing activity.

Diseases with lowered cytokine activity as referred to herein include those in which the amount of cytokine is lowered or in which the cellular response to cytokines is lowered. Examples include pressure sores, ulcers such as gastric ulcer, organofibrosis, including pulmonary fibrosis and hepatocirrhosis, osteoporosis, and diseases characterized by immune system depression, such as cancer and the like.

The cytokine activity enhancer and the medicine for diseases characterized by lowered cytokine activity of the present invention can be combined with ordinary well-known components to be formulated into compositions of various forms, such as solid, semi-solid and liquid compositions. Examples include solid compositions in the form of tablets, granules, fine granules, dispersions, powders and hard capsules; semi-solid compositions in the form of ointments, gels and creams; and liquid compositions in the form of syrups, elixirs, soft capsules, lotions, sprays and liniments.

Ordinary well-known components compatible with the present invention include, for example, hydrocarbons such as vaseline, squalane, liquid paraffin, and the like; higher alcohols such as stearyl alcohol, cetanol, and the like; lower alkyl esters of higher fatty acids such as isopropyl myristate, isopropyl palmitate, and the like; animal oils and fats such as lanolin, and the like; polyalcohols such as glycerin, propylene glycol, and the like; polyethylene glycols such as Macrogol 400, Macrogol 4000, and the like; glycerin fatty acid esters such as glycerin monostearate and the like; surfactants such as sodium laurylsulfate, polyethylene glycol monostearate, polyoxyethylene alkyl ether phosphate (trade name, NIKKOL DDP-2, produced by Nippon Surfactant Industry Co.), and the like; waxes; resins; water; and optionally preservatives such as butyl parahydroxybenzoate, methyl parahydroxybenzoate, and the like. The active ingredient of the invention can be mixed with any of these additives and can be formulated into compositions according to ordinary methods.

The compositions of the present invention may be either a single composition or a double composition, separately comprising the ethanolamine derivative of formula (I) or its salt, and cytokines or a cytokine production promoter. In the latter double compositions, the two components are combined before use. The administration routes for the two components in the double composition may be different for each component.

The content of the ethanolamine derivative of formula (I) may vary, depending on the form of the composition. Preferably, however, the content is from 0.0001 to 2% by weight of the total formulation, and more preferably from 0.001 to 1% by weight. However, in compositions intended to be diluted in use, such as bathing compositions, the content may be higher.

Where cytokine is added to lymphocytes in the above-mentioned LAK therapy, the cytokine activity enhancer of the present invention comprising an ethanolamine derivative of formula (I) may be added to the medium as an adjuvant. In this case, the amount to be added is preferably from 0.0001 to 2% by weight of the total medium, and more preferably from 0.001 to 0.5% by weight.

The cytokine activity enhancer and the formulation to treat diseases with lowered cytokine activities of the present invention can also be used as cell culture reagents for scientific studies and experiments, and also as active ingredients in ordinary medicines and cosmetics.

The formulations including cytokine activity enhancers of the present invention can also be added to lymphocytes being incubated in the above-mentioned LAK therapy. The formulations including cytokine activity enhancers can be administered orally, or by injection or endermic application.

Dosage forms for oral administration include solid preparations such as tablets, granules, powders, fine granules, hard capsules, and the like. Dosage forms may also include liquid preparations such as syrups, elixirs, soft capsules, and the like.

Tablets, granules, powders and fine granules can be prepared by mixing a compound of formula (I) or its pharmaceutically-acceptable salt with ordinary pharmaceutical additives such as lactose, starch, crystalline cellulose, magnesium stearate, hydroxypropyl cellulose, talc, and the like.

Hard capsules can be prepared by filling suitable capsules with the above-mentioned fine granules or powders.

Syrups can be prepared by dissolving or suspending a compound of formula (I) or its pharmaceutically-acceptable salt in an aqueous solution comprising sugar, D-sorbitol, carboxymethyl cellulose, and the like, together with a preservative such as methyl parahydroxybenzoate or propyl parahydroxybenzoate.

Elixirs can be prepared by mixing an ethanolic solution of a compound of formula (I) or its pharmaceutically-acceptable salt with glycerin, orange oil, lemon oil, coriander oil, anise oil, talc, and the like.

Soft capsules can be prepared by dissolving or suspending a compound of formula (I) or its pharmaceutically-acceptable salt in a lipid-based solution, such as vegetable oils, oily emulsions, glycols, and the like, and subsequentally filling soft capsules with the resulting solution or suspension.

Injectable preparations can be prepared by dissolving or emulsifying a compound of formula (I) or its pharmaceutically-acceptable salt in physiological saline or in lipid-based solutions, such as vegetable oils, oily emulsions, glycols, and the like, followed by filling ampoules or vials with the resulting solution or emulsion under germ-free conditions. Where vials are used, cytokines or a cytokine production promoter may be added along with the solution or emulsion, and the mixture may then be lyophilized.

The dosage forms for endermic application can include semi-solid preparations such as ointments, gels, creams, and the like, and liquid preparations such as lotions, liquids for cataplasms, sprays, liniments, and the like.

The medicine comprising the cytokine activity enhancer of the present invention can be administered orally or parenterally. For example, for organopathies such as organoma and cardiac disease, the cytokine activity enhancer of the invention is preferably administered orally, endermically or through injection. For epitheliopathy such as psoriasis and keloidosis, it is preferably administered endermically or through local injection.

The dose of the enhancer or medicine of the invention may vary, depending on the age and the body weight of the patient, the nature and extent of the disease, the administration route, and the amount of cytokine or cytokine production promoter to be administered along with the enhancer or formulation of the invention. In general, however, when administered to adults, the unit dose may be from 0.5 to 1000 mg of the compound of formula (I), and may be administered once to three times a day. For example, when the enhancer or formulation of the invention is systemically administered, either orally or by injection, to patients suffering from organopathy such as organoma or cardiac disease, a suitable unit dose is from 30 to 1000 mg. On the other hand, when endermically administered locally to patients suffering from organopathy or epitheliopathy, such as psoriasis or keloidosis, a suitable unit dose is from 1 to 50 mg. In these cases, the amount of cytokine or a cytokine production promoter to be administered as a medicine together with the enhancer or medicine of the invention may be decreased by from 20 to 90% of the amount generally used.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

Next, prior to illustrating examples of the present invention, test examples that demonstrate the effects of the invention are given hereinunder. The meanings of the terms as referred to in the test examples are mentioned below.

(a) MEM medium 1.2 g of sodium bicarbonate was added to 10.6 g of a minimum essential medium (10-101, produced by Dai-Nippon Pharmaceutical Co.), to which was added distilled water to make one liter. This was bubbled with carbon dioxide to have a pH of about 7. This is hereinafter referred to as MEM medium.

(b) FBS FBS means fetal bovine serum.
(c) Buffer for measurement

An aqueous solution of 50 mM Tris containing 0.2M sodium chloride, 5 mM calcium chloride and 0.05% (W/V) Brij-35 (trade name, produced by Nakarai Task Co.; polyoxyethylene (23 E.O.) lauryl ether) was adjusted to have a pH of 7.5 with hydrochloric acid added thereto at room temperature. This was used as a buffer for measurement.

(d) Collagenase

Human procollagenase as produced by anchoring-independent cells derived from human fibrosarcoma cells in a serum-free and protein-free medium was purified from the medium by CM-Sepharose (trade name, produced by Pharmacia Co.) and Zinc-Chelating Sepharose (trade name, produced by Pharmacia Co.), and then dissolved in a buffer for measurement. To this was added trypsin (Type 12, produced by Sigma Co.) as an activator. After this was incubated at 35° C. for 1 minutes, soybean trypsin inhibitor (produced by Merck & Co.,Inc.) was added thereto to inactivate the trypsin. The collagenase thus prepared was used in the following tests. (Japanese Patent Application No. 1-238941 was referred to.)

(e) Procollagenase production

In the following tests, the procollagenase production was quantified in terms of the collagenase activity as obtained through activation with trypsin.

(f) TIMP production

In the following tests, the TIMP production was quantified in terms of the collagenase inhibitory activity.

(g) βFGF response increment

It is known that βFGF promotes procollagenase production. In the following tests, therefore, the βFGF activity increment as attained by the compound added was calculated from the procollagenase production, relative to the control using purified water in place of the test compound.

(h) TGF-β1 response increment

It is known that TGF-β1 promotes TIMP production. In the following tests, therefore, the TGF-β1 activity increment as attained by the compound added was calculated from the TIMP production, relative to the control using pure water in place of the test compound.

(i) PDGF response increment

It is known that PDGF promotes procollagenase production. In the following tests, therefore, the PDGF activity increment as attained by the compound added was calculated from the procollagenage production, relative to the control using purified water in place of the test compound.

(j) βFGF response increment in animal tests

It is known that βFGF promotes vascularization. In the following animal tests, the βFGF activity increment as attained by the compound added was calculated from the amount of hemoglobin in the Matrigel as hypodermically implanted into the abdomen of a rat, relative to the control to which the test compound was not added.

Test Example 1

Normal human fibroblasts [CCD45SK (ATCC CRL 1506) as prepared from the skin of a European woman] were suspended at a cell density of $1 \times 10^5$ cells/ml in the MEM medium, comprising 10% (V/V) FBS and 1% (V/V) non-essential amino acids (produced by Dai-Nippon Pharmaceutical Co.). The suspended cells were seeded into each well of a 12-well plate in an amount of 0.8 ml/well (corresponding to $8 \times 10^4$ cells/well) and incubated in a saturated aqueous vapor with 5% $CO_2$ at 37° C.

The enhancer (N-methyl-L-serine) of cellular response to cytokines as obtained in Example 1 mentioned below was diluted with an MEM medium containing 0.6% (V/V) FBS to 1 mM, and this was used as a solution to be added to the incubated cells.

After having been incubated for 24 hours, the culture medium was removed from the plate by suction, and the cells remained were washed twice with an MEM medium containing 0.6% (v/v) (as final concentration) of FBS. Then, the cells were fed with 0.8 ml of the solution prepared above added to the cells, which were incubated for 2 days.

After the 2 days incubation, the culture medium was removed from the plate by suction, and the cells were fed with 0.8 ml of the solution and were further incubated for 2 days. This operation was repeated once again. Thus, the cells were processed in the medium containing the cytokine activity enhancer for 6 days in total.

After the above-mentioned process, the culture medium was removed from the plate by suction, and the cells were fed with 0.8 ml of an MEM medium containing 3 ng/ml of βFGF (produced by Boehringer Manheim Co.) and 0.6% (V/V) FBS, and were incubated for 3 days to obtain a culture supernatant.

3.5 ml of 10 mM Tris-HCl buffer [adjusted at pH 7.8 at 4° C., containing 1 mM calcium chloride and 0.05% (W/V) Brij-35] was added to 500 µl of the thus-obtained culture supernatant, and applied to CM-Sepharose CL-6B (trade name, produced by Pharmacia Co., having a bed volume of 0.5 ml) as previously equilibrated with the same buffer.

Next, the inhibitor was removed through treatment with 0.5 ml of the same buffer as above but containing 125 mM sodium chloride (4 times in all, 2 ml of the buffer was used in total), and the procollagenase was recovered through treatment with 0.5 ml of the same buffer as above but containing 500 mM sodium chloride (4 times in all, 2 ml of the buffer was used in total). This was used as a test sample.

The test sample was suitably diluted with a buffer for measurement (mentioned above), 25 µl of the thus-diluted sample was mixed with 25 µl of the buffer, 20 µl of a trypsin solution (as prepared by adding trypsin, Type 12 (produced by Sigma Co.) to the buffer at a concentration of 1 mg/ml) was added thereto, and this was incubated at 35° C. for 5 minutes. Then, 30 µl of a soybean trypsin inhibitor solution (as prepared at a concentration of 3 mg/ml, using the buffer) was added to this to thereby inactivate the trypsin. The resulting solution is designated collagenase solution.

Using type I collagen as labeled with fluorescein isothiocyanate (hereinafter referred to as FITC) (this is an acetic acid solution of FITC-collagen having a concentration of 1 mg/ml; produced by Cosmo-Bio Co.), as a substrate solution, the collagenase activity (unit/ml) of the solution was measured according to the method of Nagai et al. (see Inflammations, Vol. 4, No. 2, p. 123, 1984). The amount of the collagenase (derived from the procollagenase as a result of the above-mentioned trypsin treatment) that decomposed 1 µg of type I collagen (FITC-collagen) at 35° C. per one minute was referred to as 1 unit. The procollagenase production (unit/ml of culture medium) was thus obtained and referred to as $X_1$.

On the other hand, pure water was used in place of N-methyl-L-serine as Comparative Example 1, which was processed in the same manner as above. Thus, the procollagenase production (unit/ml of culture) was obtained for the control to which the cytokine activity enhancer (N-methyl-L-serine) was not added. This was referred to as $Y_1$.

Next, from these data, obtained was the cytokine (βFGF) activity increment according to the following equation. The results obtained are shown in Table 1 below.

Increment of Response to βFGF (%)=[$X_1/Y_1$]×100

TABLE 1

| Cytokine Activity Enhancer | Procollagenase Production (unit/ml) | Response to βFGF Increment (%) |
|---|---|---|
| Comparative Example 1 (purified water) | 6.8 ± 1.6 | 100 |
| Example 1 (1 mM N-Methyl-L-Serine) | 15 ± 1.0 | 220 |

Mean Value ± Standard Deviation (n = 3)

The cytokine activity enhancer of Example 1 increased the procollagenase production, that is, the Enhancer (N-Methyl-L-Serine) increase the cellular response to the cytokine(βFGF).

Test Example 2

Concentration Dependence

A cytokine activity enhancer (N-methyl-L-serine) of Example 1 mentioned below was diluted with an MEM medium containing 0.6% (V/V) FBS to be from 0.01 to 10 mM. These solutions were added to cells.

In the same manner as in Test Example 1, the cells were incubated and the culture supernatant was obtained for each solution.

The procollagenase production in each culture supernatant was quantified. The results are shown in Table 2 below.

TABLE 2

| Concentration (mM) of the Enhancer (N-Methyl-L-Serine) | Procollagenase Production (unit/ml) | Response to βFGF Increment (%) |
|---|---|---|
| Comparative Example (0 mM) | 15 ± 2.0 | 100 |
| 0.01 | 15 ± 3.3 | 100 |
| 0.1 | 17 ± 2.9 | 110 |
| 0.3 | 24 ± 3.5 | 160 |
| 1.0 | 19 ± 1.3 | 130 |
| 3.0 | 26 ± 1.5 | 170 |
| 10 | 32 ± 2.2 | 210 |

Mean Value ± Standard Deviation (n = 3)

N-methyl-L-serine increased the procollagenase production, that is, the enhancer (N-methyl-L-serine) increase the cellular response to the cytokine(βFGF) in a concentration-dependent manner.

Test Example 3

Normal human fibroblasts were seeded in the same manner as in Test Example 1.

A cytokine activity enhancer (diethanolamine) as obtained in Example 2 to be mentioned hereinafter was diluted with an MEM medium containing 0.6% (V/V) FBS to be 1 mM, and this was used as a solution to be added to the cells.

The cells were incubated in the same manner as in Test Example 1 to obtain a culture supernatant. In this, however, the amount of βFGF added was 10 ng/ml.

The results obtained by measurement are shown in Table 3 below.

TABLE 3

| Enhancer | Procollagenase Production (unit/ml) | Response to βFGF Increment (%) |
|---|---|---|
| Comparative Example 1 (purified water) | 7.3 ± 0.3 | 100 |
| Example 2 (1 mM Diethanolamine) | 14 ± 1.3 | 190 |

Mean Value ± Standard Deviation (n = 3)

The cytokine activity enhancer of Example 2 increased the procollagenase production, that is, the enhancer (Diethanolamine) increase the cellular response to the cytokine(βFGF).

Test Example 4

Normal human fibroblasts [Detroit-551 (ATCC CCL 110) as prepared from the skin of a European woman] were suspended at a cell density of 1×10$^5$ cells/ml in the MEM medium, comprising 10% (V/V) FBS, 0.1% (W/V) (as final concentration) of enzymatic hydrolysate of lactalbumin (produced by Sigma Co.), 1% (V/V) non-essential amino acids and 1 mM sodium pyruvate (both produced by Dai-Nippon Pharmaceutical Co.). The suspended cells were seeded into each well of a 12-well plate in an amount of 0.8 ml/well (corresponding to 8×10$^4$ cells/well) and incubated in a saturated aqueous vapor with 5% $CO_2$ at 37ûC.

A cytokine activity enhancer (ethanolamine) as obtained in Example 3 mentioned below was diluted with an MEM medium containing 0.6% (V/V) FBS, 0.1% (W/V) (as final concentration) of enzymatic hydrolysate of lactalbumin, 1% (V/V) non-essential amino acids and 1 mM sodium pyruvate, to be 1 mM, and this was used as a solution to be added to the incubated cells.

After having been incubated for 24 hours, the culture medium was removed from the plate by suction, and the cells remained were washed twice with the MEM medium containing 0.6% (V/V) (as final concentration) of FBS. Then, the cells were fed with 0.8 ml of the solution prepared above, and were incubated for 4 days.

After the 4 days incubation, the culture medium was removed from the plate by suction, and the cells were fed with 0.8 ml of the MEM medium containing 3 ng/ml βFGF, 0.6% (V/V) FBS, 0.1% (W/V) (as final concentration) of enzymatic hydrolysate of lactalbumin, 1% (V/V) non-essential amino acids and 1 mM sodium pyruvate, and were incubated for 3 days to obtain a culture supernatant.

1.5 ml of 10 mM Tris-HCl buffer [adjusted at pH 7.8 at 4° C., containing 1 mM calcium chloride and 0.05% (W/V) Brij-35] was added to 250 μl of the thus-obtained culture supernatant, and applied to CM-Sepharose CL-6B (trade name; having a bed volume of 0.5 ml) as previously equilibrated with the same buffer.

Next, in the same manner as in Test Example 1, procollagenase was recovered from the CM-Sepharose CL-6B (trade name), and the amount of procollagenase thus collected was measured. The results are shown in Table 4 below.

TABLE 4

| Enhancer | Procollagenase Production (unit/ml) | Response to βFGF Increment (%) |
|---|---|---|
| Comparative Example 1 (purified water) | 12 ± 1.7 | 100 |
| Example 3 (1 mM Ethanolamine) | 21 ± 1.3 | 180 |

Mean Value ± Standard Deviation (n = 3)

The cytokine activity enhancer of Example 3 increased the procollagenase production, that is, the enhancer (Ethanolamine) increase the cellular response to the cytokine(βFGF).

Test Example 5

A cytokine activity enhancer (N-methylethanolamine) as obtained in Example 4 to be mentioned hereinunder was tested for the βFGF activity increment, in the same manner as in Test Example 4. The results obtained by measurement are shown in Table 5 below.

TABLE 5

| Enhancer | Procollagenase Production (unit/ml) | Response to βFGF Increment (%) |
|---|---|---|
| Comparative Example 1 (purified water) | 6.8 ± 0.7 | 100 |
| Example 4 (1 mM N-Methylethanolamine) | 12 ± 1.7 | 180 |

Mean Value ± Standard Deviation (n = 3)

The cytokine activity enhancer of Example 4 increased the procollagenase production, that is, the enhancer (Methylethanolamine) increase the cellular response to the cytokine(βFGF).

Test Example 6

Normal human fibroblasts [Detroit-551 (ATCC CCL 110) as collected from the skin of a European woman] were suspended at a cell density of $1 \times 10^5$ cells/ml in the MEM medium (hereinafter referred to as MEM2 medium), comprising 10% (V/V) FBS, 1% (V/V) (as final concentration) of non-essential amino acids and 1 mM sodium pyruvate (both produced by Dai-Nippon Pharmaceutical Co.). The cells were seeded into each well of a 12-well plate in an amount of 0.8 ml/well (corresponding to $8 \times 10^4$ cells/well) and incubated in a saturated aqueous vapor with 5% $CO_2$ at 37° C.

A cytokine activity enhancer (Diisopropanolamine) as obtained in Example 5 mentioned below was diluted with the MEM2 medium containing 0.6% (V/V) FBS to be 3 mM, and this was used as a solution to be added to the incubated cells.

After having been incubated for 24 hours, the culture medium was removed from the plate by suction, and the cells remained were washed twice with the MEM2 medium containing 0.6% (V/V) (as final concentration) of FBS. Then, the cells were fed with 0.8 ml of the solution prepared above and were incubated for 2 days.

After the 2 days incubation, the culture was removed by filtration under suction, and 0.8 ml of the solution was again added to the remaining cells, which were then incubated for 2 days. Thus, the cells were incubated for 4 days in total.

After the additional 2 days incubation, the culture medium was removed from the plate by suction, and 0.8 ml of the MEM2 medium containing 3 ng/ml βFGF and 0.6% (V/V) FBS and were incubated for 3 days to obtain a culture supernatant.

Next, in the same manner as in Test Example 1, procollagenase was recovered from CM-Sepharose CL-6B (trade name), and the amount of procollagenase thus collected was measured.

The procollagenase production in the culture supernatant was quantified. The results are shown in Table 6 below.

TABLE 6

| Enhancer | Procollagenase Production (unit/ml) | Response to βFGF Increment (%) |
|---|---|---|
| Comparative Example 1 (purified water) | 8.6 ± 2.3 | 100 |
| Example 5 (3 mM Diisopropanolamine) | 65 ± 13 | 760 |

Mean Value ± Standard Deviation (n = 3)

Diisopropanolamine increased the procollagenase production, that is, the enhancer(N-Isopropanol-2-Methyl-Ethanolamine) increase the cellular response to the cytokine (βFGF).

Test Example 7

Normal human fibroblasts were seeded in the same manner as in Test Example 6.

A cytokine activity enhancer (D,L-2-Amino-1-Propanol) as obtained in Example 6 to be mentioned hereinafter was diluted with the MEM2 medium containing 0.6% (V/V) FBS to be 3 mM, and this was used as a solution to be added to the cells.

The cells were incubated in the same manner as in Test Example 6 to obtain a culture supernatant.

The procollagenase production in the thus-obtained culture supernatant was quantified. The results are shown in Table 7 below.

TABLE 7

| Enhancer | Procollagenase Production (unit/ml) | Response to βFGF Increment (%) |
|---|---|---|
| Comparative Example 1 (purified water) | 8.6 ± 2.3 | 100 |
| Example 6 (3 mM D,L-2-Amino-1-Propanol) | 33 ± 4.7 | 380 |

Mean Value ± Standard Deviation (n = 3)

D,L-2-Amino-1-Propanol increased the procollagenase production, that is, the enhancer (D,L-Amino-1-Propanol) increase the cellular response to the cytokine(βFGF).

Test Example 8

Normal human fibroblasts were seeded in the same manner as in Test Example 6.

A cytokine activity enhancer (2-amino-1-butanol) as obtained in Example 7 to be mentioned hereinafter was diluted with the MEM2 medium containing 0.6% (V/V) FBS to be 3 mM, and this was used as a solution to be added to the cells.

The cells were incubated in the same manner as in Test Example 6 to obtain a culture supernatant.

The procollagenase production in the thus-obtained culture supernatant was quantified. The results are shown in Table 8 below.

TABLE 8

| Enhancer | Procollagenase Production (unit/ml) | Response to βFGF Increment (%) |
|---|---|---|
| Comparative Example 1 (purified water) | 12 ± 2.2 | 100 |
| Example 7 (3 mM 2-Amino-1-Butanol) | 22 ± 2.4 | 190 |

Mean Value ± Standard Deviation (n = 3)

2-Amino-1-Butanol increased the procollagenase production, that is, the enhancer (2-Amino-1-Butanol) increase the cellular response to the cytokine(βFGF).

Test Example 9

Normal human fibroblasts were seeded in the same manner as in Test Example 6.

A cytokine activity enhancer (1,3-diamino-2-propanol) as obtained in Example 8 to be mentioned hereinafter was diluted with the MEM2 medium containing 0.6% (V/V) FBS to be 3 mM, and this was used as a solution to be added to the cells.

The cells were incubated in the same manner as in Test Example 6 to obtain a culture supernatant.

The procollagenase production in the thus-obtained culture supernatant was quantified. The results are shown in Table 9 below.

TABLE 9

| Enhancer | Procollagenase Production (unit/ml) | Response to βFGF Increment (%) |
|---|---|---|
| Comparative Example 1 (purified water) | 12 ± 2.2 | 100 |
| Example 8 (3 mM 1,3-Diamino-2-Propanol) | 18 ± 0.95 | 150 |

Mean Value ± Standard Deviation (n = 3)

1,3-Diamino-2-Propanol increased the procollagenase production, that is, the enhancer (1,3-Diamino-2-Propanol) increase the cellular response to the cytokine(βFGF).

Test Example 10

Normal human fibroblasts were seeded in the same manner as in Test Example 6.

A cytokine activity enhancer (1-amino-2-butanol) as obtained in Example 9 to be mentioned hereinafter was diluted with the MEM2 medium containing 0.6% (V/V) FBS to be 3 mM, and this was used as a solution to be added to the cells.

The cells were incubated in the same manner as in Test Example 6 to obtain a culture supernatant.

The procollagenase production in the thus-obtained culture supernatant was quantified. The results are shown in Table 10 below.

TABLE 10

| Enhancer | Procollagenase Production (unit/ml) | Response to βFGF Increment (%) |
|---|---|---|
| Comparative Example 1 (purified water) | 8.2 ± 2.0 | 100 |
| Example 9 (3 mM 1-Amino-2-Butanol) | 24 ± 2.3 | 290 |

Mean Value ± Standard Deviation (n = 3)

1-Amino-2-Butanol increased the procollagenase production, that is, the enhancer (1-Amino-2-Butanol) increase the cellular response to the cytokine(βFGF).

Test Example 11

A cytokine activity enhancer (N-methyl-L-serine) as obtained in Example 1 to be mentioned hereinafter was diluted with an MEM medium containing 0.6% (V/V) FBS to be 1 mM, and this was used as a solution to be added to cells.

Cells were incubated in the solution prepared above for 6 days, in the same manner as in Test Example 1. After the 6 days incubation, the cells were fed with 0.8 ml of an MEM medium containing 30 ng/ml PDGF-BB (produced by Austral Biologicals Co.) and 0.6% (V/V) FBS, and were incubated for further 3 days. Then, the culture supernatant was obtained.

The cytokine (PDGF) activity increment was calculated in the same manner as in Test Example 1, in accordance with the following equation in which $X_2$ indicates the procollagenase production in the supernatant of the culture to which had been added the enhancer, and $Y_2$ indicates the procollagenase production in the supernatant of the culture to which purified water was added in place of the enhancer as Comparative Example 1.

Increment (%) of Response to PDEF=$[X_2/Y_2] \times 100$

The procollagenase production in the culture supernatant obtained was quantified. The results are shown in Table 11 below.

TABLE 11

| Enhancer | Procollagenase Production (unit/ml) | Response to PDGF Increment (%) |
|---|---|---|
| Comparative Example 1 (purified water) | 0.61 ± 0.10 | 100 |
| Example 1 (1 mM N-Methyl-L-Serine) | 4.2 ± 2.0 | 690 |

Mean Value ± Standard Deviation (n = 3)

The enhancer of Example 1 increased the procollagenase production, that is, the enhancer (N-Methyl-L-Serine) increase the cellular response to the cytokine(PDEF).

Test Example 12

The enhancer (N-Methyl-L-Serine) as obtained in Example 1 to be mentioned hereinafter was diluted with the MEM medium containing 0.6% (V/V) FBS to be 1 mM, and this was used as a solution to be added to cells.

Cells were incubated in the solution prepared above for 6 days, in the same-manner as in Test Example 1. After the incubation, the culture medium was removed from the plate, and the cells were fed with 0.8 ml of the MEM medium containing 3 ng/ml TGF-β1 (produced by Austral Biologicals Co.) and 0.6% (V/V) FBS, and were incubated for further 3 days. Then, the culture supernatant was obtained.

The TIMP production in the culture supernatant thus obtained was measured in the manner as mentioned below.

First, the culture supernatant was diluted 10-fold to 1000-fold with a buffer for measurement. Each dilute was mixed with a known amount (0.24 units) of a collagenase solution in the ratio 1:1. Using FITC-collagen as the substrate, the collagenase activity of the resulting mixture was measured in the same manner as in Test Example 1. From the data thus measured, an inhibitory curve was obtained, from which was obtained the dilution magnification of the culture supernatant that exhibited 50% inhibition. The dilution magnification was referred to as the unit.

On the other hand, a control was processed in the same manner as in Test Example 1, as Comparative Example 1. The cytokine (TGF-β1) activity increment was calculated according to the following equation in which $X_3$ indicates the TIMP production in the supernatant of the culture to which had been added the cytokine activity enhancer, and $Y_3$ indicates the TIMP production in the supernatant of the culture to which purified water was added in place of the enhancer as Comparative Example 1.

Increment (%) of Response to TGF-β1=$[X_3/Y_3]\times 100$

The TIMP production in the culture supernatant obtained was quantified. The results are shown in Table 12 below.

TABLE 12

| Enhancer | TIMP Production (unit/ml) | Response to TGF-β1 Increment (%) |
|---|---|---|
| Comparative Example 1 (purified water) | 99 ± 9.0 | 100 |
| Example 1 (1 mM N-Methyl-L-Serine) | 240 ± 21 | 240 |

Mean Value ± Standard Deviation (n = 3)

The enhancer of Example 1 increased the TIMP production, that is, the enhancer (N-Methyl-L-Serine) increase the cellular response to the cytokine (TGF-β1)

Test Example 13

The enhancer (Ethanolamine) as obtained in Example 3 to be mentioned hereinafter was diluted with an MEM medium containing 0.6% FBS to be 1 mM, and this was used as a solution to be added to cells. The same process as in Test Example 12 was repeated herein to obtain a culture supernatant. In this, however, the cells were incubated in the presence of the enhancer for 4 days, and the TIMP production in the supernatant of the culture medium that had been obtained in 6 days after the addition of TGF-β1 was measured.

Thus, the TIMP production in the culture supernatant obtained was quantified. The results are shown in Table 13 below.

TABLE 13

| Enhancer | TIMP Production (unit/ml) | Response to TGF-β1 Increment (%) |
|---|---|---|
| Comparative Example 1 (purified water) | 160 ± 3.0 | 100 |
| Example 3 (1 mM Ethanolamine) | 250 ± 9.0 | 160 |

Mean Value ± Standard Deviation (n = 3)

The enhancer of Example 3 increased the TIMP production, that is, the enhancer (Ethanolamine) increase the cellular response to the cytokine (TGF-β1).

Test Example 14

A cream of Example 10 [84 mM (1 weight % (hereinafter referred wt. %) N-Methyl-L-Serine] or Example 11 [75 mM (1 wt. %) N-Isopropanol-2-Methyl-Ethanolamine] was applied every day to the shaven abdominal skin region of male SD rats (7-weeks age; body weight, 210 to 230 g; 18 to 24 rats in one group; obtained from Nippon CLEA INC.) for 21 days. Next, Matrigel (trade name; basement membrane matrix phenol red-free; Catalogue Number 40234C) containing 1 ng/ml βFGF (produced by Dai-Nippon Pharmaceutical Co.) and heparin (produced by Gibco BRL Co.) was subcutaneously implanted into the abdominal region in an amount of 1 ml/rat. After 8 days, this was taken out from each rat.

The thus-collected Matrigel was homogenized with PHYSCOTRON (trade name, produced by Nichion Irikakikai Seisakusho KK) in a phosphate buffer (containing physiological saline), and then centrifuged. The amount of hemoglobin in the resulting supernatant was measured, using Hemoglobin Test Wako (produced by Wako Pure Chemicals Co.). This was referred to as $X_4$.

On the other hand, the same process as above was repeated, except that a cream of Comparative Example 2 mentioned below was used. The amount of hemoglobin in this case where the enhancer (N-Methyl-L-Serine) was not added was measured. This was referred to as $Y_4$.

TABLE 14

| Components | Comparative Example 2 |
|---|---|
| Stearic acid | 8.0 |
| Cetanol | 2.0 |
| Glycerin monostearate, Lipophilic | 2.0 |
| Lanolin | 2.0 |
| Liquid Paraffin | 6.0 |
| Methyl Polysiloxane | 0.1 |
| Butyl Parahydroxybenzoate | 0.04 |
| Potassium Hydroxide | 0.34 |
| Concentrated Glycerin | 6.0 |
| 1,3-Butylene Glycol | 7.0 |
| Sodium cetylsulfate | 0.1 |
| Methyl Parahydroxybenzoate | 0.04 |
| Purified water | 66.38 |

The numerals in this table are by gram.

Next, from these data was obtained the Increment (%) of Response to the cytokine(βFGF) according to the following equation.

Increment (%) of Response to βFGF=$[X_4/Y_4]\times 100$

The amount of hemoglobin in the Matrigel obtained was quantified. The results are shown in Table 15 below.

TABLE 15

| Enhancer | Amount of Hemoglobin (mg) | Response to βFGF Increment (%) |
|---|---|---|
| Comparative Example 2 (Not added) | 215 ± 22 | 100 |
| Example 10 (84 mM N-Methyl-L-Serine) | 262 ± 42 | 122 |
| Example 11 (75 mM Diisopropanolamine) | 245 ± 29 | 114 |

Mean Value ± Standard Error (n = 24 in Comparative Example; n = 18 in Examples 10 and 11)

N-Methyl-L-Serine and Diisopropanolamine both increased the amount of hemoglobin, as enhancing the response to cytokine (βFGF).

Test Example 15

Skin-through Permeability Test

Male Wistar rats that had been shaven on the day before the testing were sacrificed with ether, and immediately their abdominal skins were peeled.

Creams of Use Examples 28 to 30 to be mentioned hereinafter were used as samples, and a vertical diffusion cell device as shown in FIG. 1 (produced by Kelcon Engineering Co., having an effective area of 8 cm$^2$) was used herein. In FIG. 1, 1 is a cover made of tetrafluoroethylene, 2 is a sampling mouth, 3 is a drug sample, 4 is a skin specimen, 5 is an O-ring, 6 is a receptor tank, and 7 is a stirrer.

The cell of the above-mentioned, vertical diffusion cell device was put in a thermostat filled with air at 32° C. 45 ml of an isotonic phosphate buffer (as prepared from 1.44% sodium hydrogencarbonate and 2.33% potassium dihydrogenphosphate) was put into the receptor tank, while one g of a drug sample was applied onto donor side in the skin that had been peeled off from the abdominal region of each sacrificed rat (n=3). On 1, 2, 4 and 6 hours, 0.2 ml of the buffer was sampled from the receptor tank and then immediately frozen at −20° C. and stored.

The thus-frozen sample was thawed, and then diluted with 10 mM hydrochloric acid to have a suitable concentration, and aspartylglycine (final concentration: 40 μM) was added thereto as an internal standard. As an external standard, used was a standard for amino acid analysis (AN Type) containing aspartylglycine having the same concentration, and N-methyl-L-serine, ethanolamine or N-methylethanolamine having a final concentration of 10 μM. The quantitative determination of each drug sample was carried out according to a post-column, amino acid analyzing method (lithium method) using an o-phthalaldehyde method (see Analytical Biochemistry, Vol. 96, p. 298, 1979).

Figure 2:
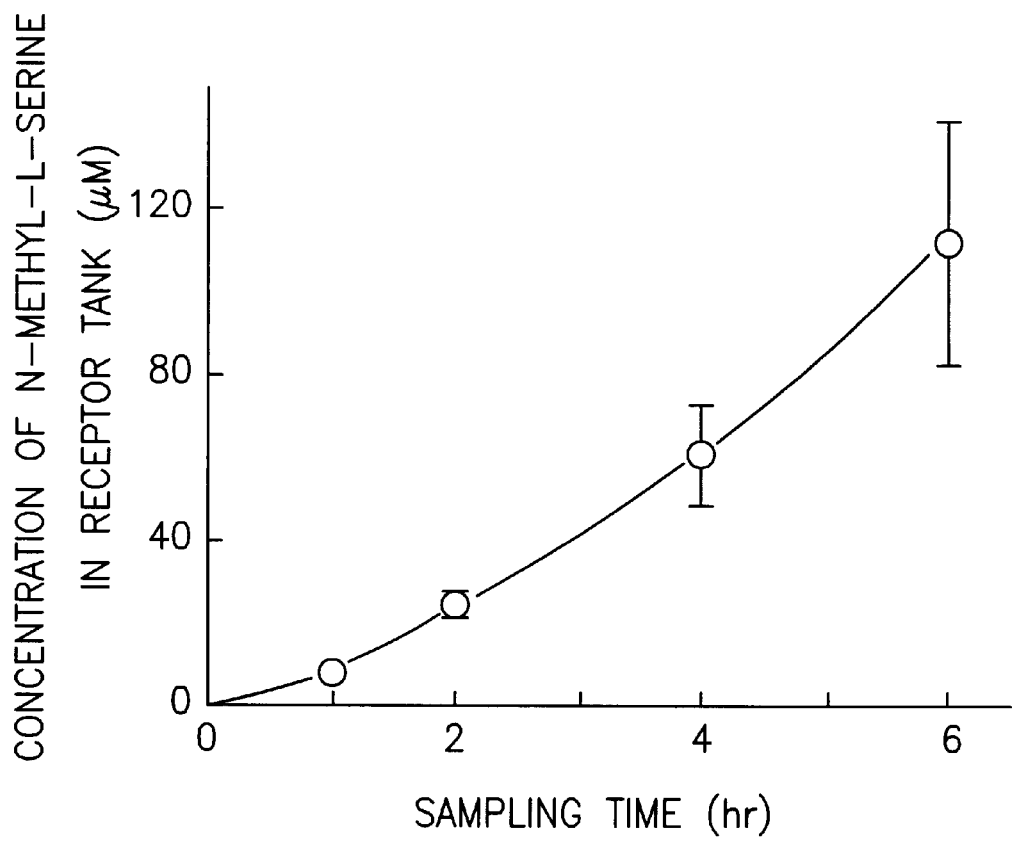
FIG. 2 shows the results of the skin-through permeability of N-methyl-L-serine as obtained in Test Example 15.

The results of the test using N-methyl-L-serine are shown in FIG. 2. N-methyl-L-serine (Use Example 28) penetrated through the rat's skin, and the skin-through penetrating rate of the compound in 2 to 6 hours after the application of the cream to the skin was about 0.12 μmol/cm$^2$/hr (see FIG. 2). In addition, it was found that Ethanolamine (Use Example 29) and N-Methylethanolamine (Use Example 30) also penetrates through the skin (see Table 16).

TABLE 16

| | Concentration of Ethanolamine or N-methylethanolamine in Receptor Tank (μmol/ml) | |
|---|---|---|
| Use Example | After 2 hours | After 6 hours |
| 29 | 0.15 | 0.63 |
| 30 | 0.18 | 0.69 |

Test Example 16

Acute Toxicity Test

Water, or an aqueous solution of N-Methyl-L-Serine (this was prepared to have a concentration of 5 g/kg of body weight of test animal, as a sample) was orally administered to male ICR mice (5 weeks-age; body weight, 24 to 28 g; 5 mice in one group), in an amount of 0.2 ml/kg of body weight. After this, the mice were observed for 7 days.

No mice of the test group to which N-Methyl-L-Serine was administered died, like those of the control group to which only water was administered.

Test Example 17

Cumulative Skin Stimulation Test

Aqueous solutions of N-Methyl-L-Serine, Ethanolamine and N-Methylethanolamine that had been adjusted to have a pH of 7 with hydrochloric acid were used as test samples.

Using Japanese native, male house rabbits (body weight: about 3 kg), the test samples were tested according to the Draize method (see Appraisal of the Safety of Chemicals in Foods, Drugs and Cosmetics, p. 46, 1959, edited and published by the Deitorial Committee, Association of Food and Drug Officials of U.S.A.).

Precisely, 0.1 ml of an aqueous 0.1% (W/V) solution of the test compound was applied to each test rabbit at its back (3×4 cm) that had been shaven, in an open condition, once a day for 4 days. 24 hours after the last application, the tested area of each rabbit was checked to score the erythema, edema, scab and rhagades, if any, formed in the area.

TABLE 17

| Evaluation | Erythema Score | Edema Score | Scab Score | Rhagades Score |
|---|---|---|---|---|
| A | 0 | 0 | 0 | 0 |
| B | 1 | 1 | 1 | 1 |
| C | 2 | 2 | 2 | 2 |
| D | 3 | 3 | 3 | 3 |

A: No erythema, no edema, no scab, and no rhagades were found.
B: Erythema, edema, scab and rhagades were found to a light degree.
C: Erythema, edema, scab and rhagades were found to a middle degree.
D: Erythema, edema, scab and rhagades were found to a heavy degree.

The erythema score, the edema score, the scab score, and the rhagades score as referred to in Table 17 were summed up to obtain the cumulative stimulation score.

Next, from the cumulative stimulation scores, obtained were the degrees of stimulation with N-Methyl-L-Serine, Ethanolamine and N-Methylethanolamine, according to the criteria shown in Table 18 below. The results are shown in Table 19 below.

TABLE 18

Stimulation to Light Degree: The cumulative stimulation score was from 0 to less than 2.
Stimulation to Middle Degree: The cumulative stimulation score was from 2 to less than 6.
Stimulation to Heavy Degree: The cumulative stimulation score was 6 or more.

TABLE 19

| Compound Tested | Cumulative Stimulation Score | Degree of Stimulation |
| --- | --- | --- |
| N-Methyl-L-Serine | 0 | Light |
| Ethanolamine | 0 | Light |
| N-Methyl-ethanolamine | 0 | Light |

It was verified that the cumulative stimulation with N-methyl-L-serine, ethanolamine and N-methylethanolamine to the skin is low.

Test Example 18

Test for Primary Stimulation to Skin—Refer to Japan Kokai Tokkyo Koho JP 04 1,130 [1992 1, 130]

Aqueous solutions of N-methyl-L-serine, ethanolamine and N-methylethanolamine that had been adjusted to have a pH 7 with hydrochloric acid were used as test samples.

Using Japanese native, male house rabbits (body weight: about 3 kg), the test samples were tested according to the above-mentioned the Draize method.

Precisely, the back of each rabbit was shaven and rubbed to form a scratched site (scratched skin). An adhesive tape for patch test (1.2×1.6 cm; Ribbon Aid, registered trade mane, produced by River Tape Chemicals Co.) as wetted with 0.1 ml of water, or 0.1 ml of an aqueous 1% (W/V) solution of the test compound was stuck onto the scratched skin and the normal skin. After 24 hours, the tape was peeled off, and the condition of the skin was observed with erythema and edema. In addition, 48 hours after the peeling of the tape, the condition of the skin was also observed. The erythema and edema, if any, formed on each skin were scored according to the criteria shown in Table 20 below.

TABLE 20

| Evaluation | Erythema Score | Edema Score |
| --- | --- | --- |
| Neither erythema nor edema was found. | 0 | 0 |
| Erythema and edema were found to a minor degree. | 1 | 1 |
| Erythema and edema were found to a light degree. | 2 | 2 |
| Erythema and edema were found to a middle degree. | 3 | 3 |
| Erythema and edema were found to a heavy degree. | 4 | 4 |

The scores as referred to in Table 21 were obtained, and the primary stimulation score was calculated according to the following equation.

Primary Stimulation Score=$[(A+B)/2]+[(C+D)/2]+[(E+F)/2]+[(G+H)/2]$

TABLE 21

A: The erythema score of the normal skin as obtained in 24 hours after the sticking of the tape to the skin.
B: The erythema score of the normal skin as obtained in 48 hours after the peeling of the tape.
C: The edema score of the normal skin as obtained in 24 hours after the sticking of the tape to the skin.
D: The edema score of the normal skin as obtained in 48 hours after the peeling of the tape.
E: The erythema score of the scratched skin as obtained in 24 hours after the sticking of the tape to the skin.
F: The erythema score of the scratched skin as obtained in 48 hours after the peeling of the tape.
G: The edema score of the scratched skin as obtained in 24 hours after the sticking of the tape to the skin.
H: The edema score of the scratched skin as obtained in 48 hours after the peeling of the tape.

Next, from the primary stimulation scores, obtained was the degree of stimulation with N-Methyl-L-Serine or Ethanolamine or N-Methylethanolamine according to the criteria shown in Table 22 below. The results are shown in Table 23 below.

TABLE 22

Stimulation to Light Degree: The primary stimulation score was from 0 to less than 2.
Stimulation to Middle Degree: The primary stimulation score was from 2 to less than 5.
Stimulation to Heavy Degree: The primary stimulation score was 5 or more.

TABLE 23

| Compound Tested | Primary Stimulation Score | Degree of Stimulation |
| --- | --- | --- |
| N-Methyl-L-Serine | 0 | Light |
| Ethanolamine | 0 | Light |
| N-Methyl-ethanolamine | 0.25 | Light |

It was verified that the stimulation with N-Methyl-L-Serine, Ethanolamine and N-Methylethanolamine to the skin is low (refer to Japan Kokai Tokkyo Koho J.P. 04 1,130 [1992 1,130]).

Test Example 19

Skin Stimulation Test

Aqueous solutions of N-methyl-L-serine, ethanolamine and N-methylethanolamine that had been adjusted to have a pH 7 with hydrochloric acid were used as test samples. These test samples were applied to 19 healthy panelists.

Precisely, according to a closed patch test (see Journal of the Society of Cosmetic Chemist, Vol. 31, p. 97, 1980) using a KI chamber, a patch with 0.05 ml of an aqueous 1% (W/V) solution of the test sample was applied to each panelist at the forearm area, which was kept closed as such for 24 hours. One hour and 24 hours after the removal of the patch, the condition of the skin of each panelist was observed.

In these patch tests using N-methyl-L-serine, ethanolamine and N-methylethanolamine, only one panelists had minor erythema in one hour and 24 hours after the removal of the patch. Thus, the test results verified that the compounds tested herein are almost not stimulative to the skin.

The following examples are to further illustrate the present invention.

EXAMPLE 1

N-Methyl-L-Serine

An aqueous solution of 1M N-methyl-L-serine was filtered to be sterilized through a nitrocellulose membrane having a pore size of 0.2 μm (DISMIC-25, produced by Advantec Toyo Co.) to obtain a cytokine activity enhancer.

EXAMPLES 2 to 4

Diethanolamine, Ethanolamine, and N-Methylethanolamine

In the same manner as in Example 1, except that solutions of 1M diethanolamine, ethanolamine or N-methylethanolamine that had been adjusted to have a pH 7.5 with hydrochloric acid were used and processed under the cooling condition in ice, cytokine activity enhancers were obtained.

EXAMPLES 5 to 9

Diisopropanolamine, D,L-2-Amino-1-Propanol, 2-Amino-1-Butanol, 1,3-Diamino-2-Propanol, and 1-Amino-2-Butanol Solutions of 1M Diisopropanolamine, D,L-2-Amino-1-Propanol, 2-Amino-1-Butanol, 1,3-Diamino-2-Propanol, or 1-Amino-2-Butanol were prepared with hydrochloric acid to have a pH 7.5 under the cooling condition in ice, and filtered to be sterilized through a nitrocellulose membrane having a pore size of 0.2 μm (DISMIC-25, produced by Advantec Toyo Co.) to obtain the enhancers.

EXAMPLES 10 and 11

Creams

Creams were prepared as in Table 24 below, containing, as the active ingredient, 1000 mg, based on 100 g of the cream, of N-Methyl-L-Serine (Example 1) or Diisopropanol-amine (Example 5).

TABLE 25

|  | Example | |
| --- | --- | --- |
| Components | 10 | 11 |
| Cytokine activity enhancer of Example 1 (N-Methyl-L-Serine) | 9.4 | 0 |
| Cytokine activity enhancer of Example 5 (Diisopropanolamine) | 0 | 7.5 |
| Stearic Acid | 8.0 | 8.0 |
| Cetanol | 2.0 | 2.0 |
| Glycerin Monostearate, Lipophilic | 2.0 | 2.0 |
| Lanolin | 2.0 | 2.0 |
| Liquid Paraffin | 6.0 | 6.0 |
| Methyl Polysiloxane | 0.1 | 0.1 |
| Butyl Parahydroxybenzoate | 0.04 | 0.04 |
| Potassium Hydroxide | 0.34 | 0 |
| Concentrated Glycerin | 6.0 | 6.0 |
| 1,3-Butylene Glycol | 7.0 | 7.0 |
| Sodium Cetylsulfate | 0.1 | 0.1 |
| Methyl Parahydroxybenzoate | 0.04 | 0.04 |
| Hydrochloric Acid | 0 | 0.4 |
| Purified water | 56.98 | 58.82 |

The numerals in the table are by gram.

Precisely, N-Methyl-L-Serine or Diisopropanolamine was mixed under heat with Methyl Parahydroxybenzoate, Potassium Hydroxide, Concentrated Glycerin, 1,3-Butylene Glycol, Sodium Cetylsulfate and purified water, in a water bath at 80° C. The resulting mixture was gradually added to a mixture of Stearic Acid, Cetanol, glycerin monostearate lipophilic, Lanolin, Liquid Paraffin, Methyl Polysiloxane and Butyl Parahydroxybenzoate, which had been heated at 80° C., with stirring them. Next, the mixture was homogenized at 2500 rpm by a homogenizer (produced by Tokushu Kikai Kogyo KK) for 2.5 minutes to thereby fully emulsify and disperse the components. Then, this was gradually cooled, with stirring, to obtain a cream.

Comparative Example 2

A cream of Comparative Example 2 was prepared in the same manner as in Examples 10 and 11, except that neither N-methyl-serine nor Diisopropanolamine was added and that purified water was added to an amount of 66.38 g.

EXAMPLES 12 to 14

Tablets

A solution of the component (2) in Table 25 below as dissolved in 30 g of water was added to a mixture of the components (A), and fully kneaded. The resulting mixture was passed through a 20-mesh sieve to prepare granules, which were then dried. The component (C) was mixed with the resulting granules and formed into tablets of 200 mg each. One tablet contained 100 mg of the active ingredient.

TABLE 26

|  |  | Example | | |
| --- | --- | --- | --- | --- |
| Components | | 12 | 13 | 14 |
| A | N-Methyl-L-Serine | 50 | 0 | 0 |
|  | Diethanolamine HCl | 0 | 50 | 0 |
|  | Ethanolamine HCl | 0 | 0 | 50 |
|  | Lactose | 10 | 10 | 10 |
|  | Corn Starch | 30 | 30 | 30 |
|  | Microcrystalline Cellulose | 8 | 8 | 8 |
| B | Hydroxypropylcellulose | 1 | 1 | 1 |
| C | Magnesium Stearate | 1 | 1 | 1 |

The numerals in the table are by gram.

EXAMPLES 15 to 20

Capsules

The components shown in Table 26 below were fully mixed, and the resulting mixture was encapsulated into No. 2 capsules in an amount of 300 mg/capsule. The capsules thus prepared contained 100 mg/capsule (Examples 15 to 17) or 200 mg/capsule (Examples 18 to 20) of the active ingredient.

TABLE 26

|  | Example | | | | | |
| --- | --- | --- | --- | --- | --- | --- |
| Components | 15 | 16 | 17 | 18 | 19 | 20 |
| N-Methyl-L-Serine | 100 | 0 | 0 | 200 | 0 | 0 |
| Diethanolamine HCl | 0 | 100 | 0 | 0 | 200 | 0 |
| Ethanolamine HCl | 0 | 0 | 100 | 0 | 0 | 200 |

TABLE 26-continued

|  | Example | | | | | |
| Components | 15 | 16 | 17 | 18 | 19 | 20 |
| --- | --- | --- | --- | --- | --- | --- |
| Lactose | 100 | 100 | 100 | 20 | 20 | 20 |
| Corn Starch | 50 | 50 | 50 | 30 | 30 | 30 |
| Microcrystalline Cellulose | 47 | 47 | 47 | 47 | 47 | 47 |
| Magnesium Stearate | 3 | 3 | 3 | 3 | 3 | 3 |

The numerals in the table are by gram.

EXAMPLES 21 to 26

Granules

The component (B) in Table 27 below as dissolved in 1000 g of water was added to a mixture of the components (A), and fully kneaded. The resulting mixture was passed through a 20-mesh sieve to prepare granules, which were then dried and dressed. Thus were obtained granules containing 30 mg/g (Examples 21 to 23) or 300 mg/g (Examples 24 to 26) of the active ingredient.

TABLE 27

|  |  | Example | | | | | |
| | Components | 21 | 22 | 23 | 24 | 25 | 26 |
| --- | --- | --- | --- | --- | --- | --- | --- |
| A | N-Methyl-L-Serine | 30 | 0 | 0 | 300 | 0 | 0 |
|  | Diethanol-amine HCl | 0 | 30 | 0 | 0 | 300 | 0 |
|  | Ethanolamine HCl | 0 | 0 | 30 | 0 | 0 | 300 |
|  | Lactose | 470 | 470 | 470 | 470 | 470 | 470 |
|  | Corn Starch | 470 | 470 | 470 | 200 | 200 | 200 |
| B | Hydroxy-propyl-cellulose | 30 | 30 | 30 | 30 | 30 | 30 |

The numerals in the table are by gram.

EXAMPLES 27 to 29

Syrups

The components (B) in Table 28 below were dissolved in 400 ml of purified water at 90° C., then the component (C) was added thereto at the same temperature, and the whole was fully mixed and then cooled to 30° C. The component (A) as dissolved in 100 ml of purified water was added to the resulting mixture, and stirred at 30° C. for 30 minutes. Next, the components (D) were added thereto and stirred for 20 minutes, to which was added purified water to make 1000 ml. The resulting mixture was filtered to be sterilized to obtain a syrup containing 100 mg/ml of the active ingredient.

TABLE 28

|  |  | Example | | |
| | Components | 27 | 28 | 29 |
| --- | --- | --- | --- | --- |
| A | N-Methyl-L-Serine | 100 | 0 | 0 |
|  | Diethanolamine HCl | 0 | 100 | 0 |
|  | Ethanolamine HCl | 0 | 0 | 100 |
| B | Methyl Parahydroxybenzoate | 0.3 | 0.3 | 0.3 |
|  | Propyl | 0.15 | 0.15 | 0.15 |

TABLE 28-continued

|  |  | Example | | |
| | Components | 27 | 28 | 29 |
| --- | --- | --- | --- | --- |
|  | Parahydroxybenzoate Sugar | 300 | 300 | 300 |
| C | Aqueous solution of 70% (W/V) D-sorbitol | 250 | 250 | 250 |
| D | Sodium Citrate | 10 | 10 | 10 |
|  | Citric Acid | 1.5 | 1.5 | 1.5 |

Pure water was added to make 1000 ml in total.
The numerals in the table are by gram.

EXAMPLES 30 to 53

Injections

The enhancer of cellular response to cytokines shown in Table 29 below was dissolved in purified water for injection (containing 10% human serum albumin and 20% mannitol) to prepare a solution of 200 ml, which was then filtered to be sterilized. For N-Methyl-L-Serine, Ethanolamine and Diethanolamine, the sterilized solution of the enhancer was filled into 10-ml vials in an amount of 2 ml/vial. In a germ-free condition, the vials were substituted with nitrogen and sealed to obtain injections. For N-Methylethanolamine, Diisopropanolamine, D,L-2-Amino-1-Propanol, 2-Amino-1-Butanol, 1,3-Diamino-2-Propanol and 1-Amino-2-Butanol, the sterilized solution of the enhancer was filled into 3-ml brown ampules in an amount of 2 ml/ampule. The ampules were hot-sealed to obtain injections. The amount of the active ingredient shown in the table indicates the amount of N-Methyl-L-Serine, Ethanolamine, Diethanolamine, N-Methylethanolamine, Diisopropanolamine, D,L-2-Amino-1-Propanol, 2-Amino-1-Butanol, 1,3-Diamino-2-Propanol or 1-Amino-2-Butanol in one vial or ampule.

TABLE 29

| Example | Enhancer | Amount Mixed | Amount of Active Ingredient |
| --- | --- | --- | --- |
| 30 | N-Methyl-L-Serine | 10 g | 100 mg |
| 31 | N-Methyl-L-Serine TGF-β1 | 10 g 1 mg | 100 mg |
| 32 | Diethanolamine HCl | 40 g | 400 mg |
| 33 | Diethanolamine TGF-β1 | 40 g 10 μg | 400 mg |
| 34 | Ethanolamine HCl | 20 g | 200 mg |
| 35 | Ethanolamine HCl TGF-β1 | 20 g 100 μg | 200 mg |
| 36 | N-Methylethanolamine | 10 g | 100 mg |
| 37 | " | 20 g | 200 mg |
| 38 | " | 40 g | 400 mg |
| 39 | Diisopropanolamine | 10 g | 100 mg |
| 40 | " | 20 g | 200 mg |
| 41 | " | 40 g | 400 mg |
| 42 | D,L-2-Amino-1-Propanol | 10 g | 100 mg |
| 43 | " | 20 g | 200 mg |
| 44 | " | 40 g | 400 mg |
| 45 | 2-Amino-1-Butanol | 10 g | 100 mg |
| 46 | " | 20 g | 200 mg |
| 47 | " | 40 g | 400 mg |
| 48 | 1,3-Diamino-2-Propanol | 10 g | 100 mg |
| 49 | " | 20 g | 200 mg |
| 50 | " | 40 g | 400 mg |
| 51 | 1-Amino-2-Butanol | 10 g | 100 mg |
| 52 | " | 20 g | 200 mg |
| 53 | " | 40 g | 400 mg |

EXAMPLES 54 to 71

Ointments

The components (A) in Table 30 and 31 were mixed under heat in a water bath at 80° C., and the resulting mixture was gradually added, with stirring, to a mixture of the components (B) that had been heated at 80° C. Next, this was homogenized at 2500 rpm by a homogenizer (produced by Tokushu Kikai Kogyo KK) for 2.5 minutes to thereby fully emulsify and disperse the components, and thereafter gradually cooled still with stirring. Finally, the ethanolamine derivative, and βFGF or αFGF were added thereto to obtain ointments containing 500 mg/100 g of the active ingredient and 2 mg/100 g of βFGF (Examples 54 to 62) or containing 1000 mg/100 g of the active ingredient and 0.2 mg/100 g of αFGF (Examples 63 to 71).

TABLE 30

| | | Example | | | | | | | | |
|---|---|---|---|---|---|---|---|---|---|---|
| | Components | 54 | 55 | 56 | 57 | 58 | 59 | 60 | 61 | 62 |
| Active Ingredient | Example 1 N-Methyl-L-Serine | 4.7 | 0 | 0 | 0 | 0 | 0 | 0 | 0 | 0 |
| | Example 2 Diethanolamine | 0 | 5.3 | 0 | 0 | 0 | 0 | 0 | 0 | 0 |
| | Example 3 Ethanolamine | 0 | 0 | 8.7 | 0 | 0 | 0 | 0 | 0 | 0 |
| | Example 4 N-Methyl-ethanolamine | 0 | 0 | 0 | 7.2 | 0 | 0 | 0 | 0 | 0 |
| | Example 5 Disopropanolamine | 0 | 0 | 0 | 0 | 3.8 | 0 | 0 | 0 | 0 |
| | Example 6 D,L-2-Amino-1-Propanol | 0 | 0 | 0 | 0 | 0 | 6.6 | 0 | 0 | 0 |
| | Example 7 2-Amino-1-Butanol | 0 | 0 | 0 | 0 | 0 | 0 | 6.1 | 0 | 0 |
| | Example 8 1,3-Diamino-2-Propanol | 0 | 0 | 0 | 0 | 0 | 0 | 0 | 6.0 | 0 |
| | Example 9 1-Amino-2-Butanol | 0 | 0 | 0 | 0 | 0 | 0 | 0 | 0 | 6.1 |
| A | Methyl Parahydroxy-benzoate | 0.1 | 0.1 | 0.1 | 0.1 | 0.1 | 0.1 | 0.1 | 0.1 | 0.1 |
| | Propylene Glycol | 6.7 | 6.7 | 6.7 | 6.7 | 6.7 | 6.7 | 6.7 | 6.7 | 6.7 |
| | Purified water | 39.398 | 38.798 | 35.398 | 36.898 | 40.298 | 37.498 | 37.998 | 38.098 | 37.998 |
| B | Squalane | 4.7 | 4.7 | 4.7 | 4.7 | 4.7 | 4.7 | 4.7 | 4.7 | 4.7 |
| | White Petrolatum | 24 | 24 | 24 | 24 | 24 | 24 | 24 | 24 | 24 |
| | Stearyl Alcohol | 8.7 | 8.7 | 8.7 | 8.7 | 8.7 | 8.7 | 8.7 | 8.7 | 8.7 |
| | Isopropyl Myristate | 6.0 | 6.0 | 6.0 | 6.0 | 6.0 | 6.0 | 6.0 | 6.0 | 6.0 |
| | Polyethyleneglycol Monostearate[1] | 1.3 | 1.3 | 1.3 | 1.3 | 1.3 | 1.3 | 1.3 | 1.3 | 1.3 |
| | Polyoxyethylene Alkyl Ether Phosphate[2] | 2.3 | 2.3 | 2.3 | 2.3 | 2.3 | 2.3 | 2.3 | 2.3 | 2.3 |
| | Glycerin Monostearate | 2.0 | 2.0 | 2.0 | 2.0 | 2.0 | 2.0 | 2.0 | 2.0 | 2.0 |
| | Butyl Parahydroxy-benzoate | 0.1 | 0.1 | 0.1 | 0.1 | 0.1 | 0.1 | 0.1 | 0.1 | 0.1 |
| bFGF | | 0.002 | 0.002 | 0.002 | 0.002 | 0.002 | 0.002 | 0.002 | 0.002 | 0.002 |
| aFGF | | — | — | — | — | — | — | — | — | — |

[1] Nikkol MYS-45 (trade name), produced by Nippon Surfactant Industry C0.
[2] Nikkol DDP-2 (trade name), produced by Nippon Surfactant Industry C0.
The numerals in the table are by gram.

TABLE 31

| | | Example | | | | | | | | |
|---|---|---|---|---|---|---|---|---|---|---|
| | Components | 63 | 64 | 65 | 66 | 67 | 68 | 69 | 70 | 71 |
| Active Ingredient | Example 1 N-Methyl-L-Serine | 9.4 | 0 | 0 | 0 | 0 | 0 | 0 | 0 | 0 |
| | Example 2 Diethanolamine | 0 | 10.5 | 0 | 0 | 0 | 0 | 0 | 0 | 0 |
| | Example 3 Ethanolamine | 0 | 0 | 17.4 | 0 | 0 | 0 | 0 | 0 | 0 |
| | Example 4 N-Methyl-ethanolamine | 0 | 0 | 0 | 14.3 | 0 | 0 | 0 | 0 | 0 |
| | Example 5 Disopropanol-amine | 0 | 0 | 0 | 0 | 7.5 | 0 | 0 | 0 | 0 |
| | Example 6 | 0 | 0 | 0 | 0 | 0 | 13.3 | 0 | 0 | 0 |

TABLE 31-continued

|   | Components | \multicolumn{9}{c|}{Example} |
|---|---|---|---|---|---|---|---|---|---|---|
|   |   | 63 | 64 | 65 | 66 | 67 | 68 | 69 | 70 | 71 |
|   | D,L-2-Amino-1-propanol Example 7 | 0 | 0 | 0 | 0 | 0 | 0 | 12.2 | 0 | 0 |
|   | 2-Amino-1-Butanol Example 8 | 0 | 0 | 0 | 0 | 0 | 0 | 0 | 12.1 | 0 |
|   | 1,3-Diamino-2-Propanol Example 9 | 0 | 0 | 0 | 0 | 0 | 0 | 0 | 0 | 12.2 |
| A | 1-Amino-2-Butanol Methyl Parahydroxy-benzoate | 0.1 | 0.1 | 0.1 | 0.1 | 0.1 | 0.1 | 0.1 | 0.1 | 0.1 |
|   | Propylene Glycol | 6.7 | 6.7 | 6.7 | 6.7 | 6.7 | 6.7 | 6.7 | 6.7 | 6.7 |
|   | Purified water | 34.6998 | 33.5998 | 26.6998 | 29.7998 | 36.5998 | 30.7998 | 31.8998 | 31.9998 | 31.8998 |
| B | Squalane | 4.7 | 4.7 | 4.7 | 4.7 | 4.7 | 4.7 | 4.7 | 4.7 | 4.7 |
|   | White Petrolatum | 24 | 24 | 24 | 24 | 24 | 24 | 24 | 24 | 24 |
|   | Stearyl Alcohol | 8.7 | 8.7 | 8.7 | 8.7 | 8.7 | 8.7 | 8.7 | 8.7 | 8.7 |
|   | Isopropyl Myristate | 6.0 | 6.0 | 6.0 | 6.0 | 6.0 | 6.0 | 6.0 | 6.0 | 6.0 |
|   | Polyethyleneglycol Monostearate[1] | 1.3 | 1.3 | 1.3 | 1.3 | 1.3 | 1.3 | 1.3 | 1.3 | 1.3 |
|   | Polyoxyethylene Alkyl Ether Phosphate[2] | 2.3 | 2.3 | 2.3 | 2.3 | 2.3 | 2.3 | 2.3 | 2.3 | 2.3 |
|   | Glyceryl Monostearate | 2.0 | 2.0 | 2.0 | 2.0 | 2.0 | 2.0 | 2.0 | 2.0 | 2.0 |
|   | Butyl Parahydroxy-benzoate | 0.1 | 0.1 | 0.1 | 0.1 | 0.1 | 0.1 | 0.1 | 0.1 | 0.1 |
| bFGF |   | — | — | — | — | — | — | — | — | — |
| aFGF |   | 0.0002 | 0.0002 | 0.0002 | 0.0002 | 0.0002 | 0.0002 | 0.0002 | 0.0002 | 0.0002 |

[1] NIKKOL MYS-45 (trade name), produced by Nippon Surfactant Industry Co.
[2] NIKKOL DDP-2 (trade name), produced by Nippon Surfactant Industry Co.
The numerals in the table are by gram.

Use examples are mentioned below, in which, unless otherwise specifically indicated, the numerals are by wt. %.

Use Examples 1 to 27

Lotions were prepared as in Tabled 32 and 33 below, containing, as the active ingredient, 100, 200 or 400 mg, based on 100 g of the lotion, of N-Methyl-L-Serine (Use Examples 1, 10 and 19), Diethanolamine (Use Examples 2, 11 and 20), Ethanolamine (Use Examples 3, 12 and 21), N-Methylethanolamine (Use Examples 4, 13 and 22), Disopropanolamine (Use Examples 5, 14 and 23), D,L-2-Amino-1-Propanol (Use Examples 6, 15 and 24), 2-Amino-1-Butanol (Use Examples 7, 16 and 25), 1,3-Diamino-2-Propanol (Use Examples 8, 17 and 26), or 1-Amino-2-Butanol (Use Examples 9, 18 and 27).

TABLE 32

|   |   | \multicolumn{14}{c|}{Use Example} |
|---|---|---|---|---|---|---|---|---|---|---|---|---|---|---|---|
|   | Components | 1 | 2 | 3 | 4 | 5 | 6 | 7 | 8 | 9 | 10 | 11 | 12 | 13 | 14 |
| Active Ingredient | Example 1 N-Methyl-L-Serine | 0.94 | 0 | 0 | 0 | 0 | 0 | 0 | 0 | 0 | 1.88 | 0 | 0 | 0 | 0 |
|   | Example 2 Diethanolamine | 0 | 1.05 | 0 | 0 | 0 | 0 | 0 | 0 | 0 | 0 | 2.10 | 0 | 0 | 0 |
|   | Example 3 Ethanolamine | 0 | 0 | 1.74 | 0 | 0 | 0 | 0 | 0 | 0 | 0 | 0 | 3.48 | 0 | 0 |
|   | Example 4 N-Methyl-ethanolamine | 0 | 0 | 0 | 1.43 | 0 | 0 | 0 | 0 | 0 | 0 | 0 | 0 | 2.87 | 0 |
|   | Example 5 Disopropanol-amine | 0 | 0 | 0 | 0 | 0.75 | 0 | 0 | 0 | 0 | 0 | 0 | 0 | 0 | 1.50 |
|   | Example 6 D,L-2-Amino-1-Propanol | 0 | 0 | 0 | 0 | 0 | 1.30 | 0 | 0 | 0 | 0 | 0 | 0 | 0 | 0 |
|   | Example 7 2-Amino-1-Bropanol | 0 | 0 | 0 | 0 | 0 | 0 | 1.22 | 0 | 0 | 0 | 0 | 0 | 0 | 0 |
|   | Example 8 1,3-Diamino-2- | 0 | 0 | 0 | 0 | 0 | 0 | 0 | 1.21 | 0 | 0 | 0 | 0 | 0 | 0 |

TABLE 32-continued

|   | Components | \multicolumn{14}{c}{Use Example} |
|---|---|---|---|---|---|---|---|---|---|---|---|---|---|---|---|
|   |   | 1 | 2 | 3 | 4 | 5 | 6 | 7 | 8 | 9 | 10 | 11 | 12 | 13 | 14 |
|   | Propanol |   |   |   |   |   |   |   |   |   |   |   |   |   |   |
|   | Example 9 1-Amino-2-Butanol | 0 | 0 | 0 | 0 | 0 | 0 | 0 | 0 | 1.22 | 0 | 0 | 0 | 0 | 0 |
| A | Sodium Laurate | 0.5 | 0.5 | 0.5 | 0.5 | 0.5 | 0.5 | 0.5 | 0.5 | 0.5 | 0.5 | 0.5 | 0.5 | 0.5 | 0.5 |
|   | Purifiedwater | 91.96 | 91.85 | 91.16 | 91.47 | 92.15 | 91.60 | 91.68 | 91.69 | 91.68 | 91.02 | 90.80 | 89.42 | 90.03 | 91.40 |
| B | Bleached Beeswax | 0.1 | 0.1 | 0.1 | 0.1 | 0.1 | 0.1 | 0.1 | 0.1 | 0.1 | 0.1 | 0.1 | 0.1 | 0.1 | 0.1 |
|   | Cetanol[1] | 1.5 | 1.5 | 1.5 | 1.5 | 1.5 | 1.5 | 1.5 | 1.5 | 1.5 | 1.5 | 1.5 | 1.5 | 1.5 | 1.5 |
|   | Concentrated Glycerin | 5.0 | 5.0 | 5.0 | 5.0 | 5.0 | 5.0 | 5.0 | 5.0 | 5.0 | 5.0 | 5.0 | 5.0 | 5.0 | 5.0 |

[1]Pinasol NAA 48 (trade name, produced by Nippon Oils & Fats Co.).
The numerals in the table are by gram.

TABLE 33

|   | Components | \multicolumn{13}{c}{Use Example} |
|---|---|---|---|---|---|---|---|---|---|---|---|---|---|---|
|   |   | 15 | 16 | 17 | 18 | 19 | 20 | 21 | 22 | 23 | 24 | 25 | 26 | 27 |
| Active Ingredient | Example 1 N-Methyl-L-Serine | 0 | 0 | 0 | 0 | 3.76 | 0 | 0 | 0 | 0 | 0 | 0 | 0 | 0 |
|   | Example 2 Diethanolamine | 0 | 0 | 0 | 0 | 0 | 4.21 | 0 | 0 | 0 | 0 | 0 | 0 | 0 |
|   | Example 3 Ethanolamine | 0 | 0 | 0 | 0 | 0 | 0 | 6.96 | 0 | 0 | 0 | 0 | 0 | 0 |
|   | Example 4 N-Methyl-ethanolamine | 0 | 0 | 0 | 0 | 0 | 0 | 0 | 5.73 | 0 | 0 | 0 | 0 | 0 |
|   | Example 5 Disopropanol-amine | 0 | 0 | 0 | 0 | 0 | 0 | 0 | 0 | 3.00 | 0 | 0 | 0 | 0 |
|   | Example 6 D,L-2-Amino-1-Propanol | 2.70 | 0 | 0 | 0 | 0 | 0 | 0 | 0 | 0 | 5.30 | 0 | 0 | 0 |
|   | Example 7 2-Amino-1-Butanol | 0 | 2.44 | 0 | 0 | 0 | 0 | 0 | 0 | 0 | 0 | 3.66 | 0 | 0 |
|   | Example 8 1,3-Diamino-2-Propanol | 0 | 0 | 2.42 | 0 | 0 | 0 | 0 | 0 | 0 | 0 | 0 | 3.63 | 0 |
|   | Exampie 9 1-Amino-2-Butanol | 0 | 0 | 0 | 2.44 | 0 | 0 | 0 | 0 | 0 | 0 | 0 | 0 | 3.66 |
| A | Sodium Laurate | 0.5 | 0.5 | 0.5 | 0.5 | 0.5 | 0.5 | 0.5 | 0.5 | 0.5 | 0.5 | 0.5 | 0.5 | 0.5 |
|   | Purified water | 90.20 | 90.46 | 90.48 | 90.46 | 89.14 | 88.69 | 85.94 | 87.17 | 89.90 | 87.60 | 89.24 | 89.27 | 89.24 |
| B | Bleached Beeswax | 0.1 | 0.1 | 0.1 | 0.1 | 0.1 | 0.1 | 0.1 | 0.1 | 0.1 | 0.1 | 0.1 | 0.1 | 0.1 |
|   | Cetanol[1] | 1.5 | 1.5 | 1.5 | 1.5 | 1.5 | 1.5 | 1.5 | 1.5 | 1.5 | 1.5 | 1.5 | 1.5 | 1.5 |
|   | Concentrated Glycerin | 5.0 | 5.0 | 5.0 | 5.0 | 5.0 | 5.0 | 5.0 | 5.0 | 5.0 | 5.0 | 5.0 | 5.0 | 5.0 |

[1]Pinasol NAA 48 (trade name, produced by Nippon Oils & Fats Co.).
The numerals in the table are by gram.

Precisely, the active ingredient indicated in the above-mentioned table was mixed with the components (A) under heat in a water bath at 80° C. On the other hand, the components (B) were mixed also under heat at 80° C. The former mixture was gradually added to the latter mixture, with stirring, and then homogenized at 2500 rpm by a homogenizer (produced by Tokushu Kikai Kogyo KK) for 2.5 minutes. This was gradually cooled to room temperature still with stirring to obtain a lotion.

Use Examples 28 to 30

Creams as in Table 34 below were prepared.

TABLE 34

|   | Components | \multicolumn{3}{c}{Use Example} |
|---|---|---|---|---|
|   |   | 28 | 29 | 30 |
| A | Cetanol | 3 | 3 | 3 |
|   | Glycerin Monostearate, | 2.5 | 2.5 | 2.5 |

TABLE 34-continued

| Components | Use Example 28 | Use Example 29 | Use Example 30 |
|---|---|---|---|
| Lipophilic Polyoxyethylene Cetyl-ether (20 E.O.) | 1.5 | 1.5 | 1.5 |
| Liquid paraffin | 10 | 10 | 10 |
| Glycerin tri-2-ethylhexanoate | 5 | 5 | 5 |
| Methyl Polysiloxane | 1 | 1 | 1 |
| B Butyl Parahydroxybenzoate | 0.1 | 0.1 | 0.1 |
| C Methyl parahydroxybenzoate | 0.15 | 0.15 | 0.15 |
| Disodium Edetate | 0.1 | 0.1 | 0.1 |
| D Sodium N-Stearoyl-L-Glutamate | 0.9 | 0.9 | 0.9 |
| Dipropylene glycol | 5 | 5 | 5 |
| N-Methyl-L-serine | 2 | 0 | 0 |
| Ethanolamine | 0 | 2 | 0 |
| N-Methylethanolamine | 0 | 0 | 2 |
| Water | balance | balance | balance |
| Total | 100 | 100 | 100 |

The numerals in the table are by wt. %.

Precisely, the components (A) were uniformly mixed and melted at 80° C., and the component (B) was added thereto and melted (Mixture I). Apart from this, the components (D) were uniformly mixed and melted at 80° C., and the components (C) were added thereto and melted (Mixture II). Next, Mixture II was gradually added to Mixture I and cooled to 30° C., with fully stirring, to obtain a cream.

Use Example 31

Hair Tonic

TABLE 35

| | |
|---|---|
| Salicylic Acid | 0.1 |
| Diethanolamine | 0.01 |
| Propylene Glycol | 3.0 |
| Glycyrrhetinic Acid | 0.01 |
| 1-Menthol | 0.1 |
| Ethanol | 50.0 |
| Human PDGF (produced by Collaborative Res. Inc.; aqueous 0.01% solution) | 0.05 |
| Fragrance | ad lib. |
| Purified Water | balance |
| | 100 wt. % |

Use Example 32

Hair Tonic

TABLE 36

| | |
|---|---|
| N-Methyl-L-Serine | 0.1 |
| Ethanolamine | 0.001 |
| Ethanol | 4.0 |
| Isopropanol | 1.0 |
| Fragrance, Preservative | ad lib. |
| Purified water | balance |
| | 100 wt. % |

Use Example 33 (Aerosol-type Filming Agent):

Use Example 33

Aerosol-type Filming Agent

TABLE 37

| | |
|---|---|
| Ethylcellulose | 7.5 |
| N-Methyl-L-Serine | 0.2 |
| Glycerin | 1.0 |
| 1-Menthol | 0.3 |
| Ethanol | 30.98 |
| Human PDGF (produced by Collaborative Res. Inc.; aqueous 0.01% solution) | 0.02 |
| Propellant (Dimethyl Ether) | 60.0 |
| | 100 wt. % |

Use Example 34 (Bath Salt):

Use Example 34

Bath Salt 3 g of N-methyl-L-serine was mixed with the following components to obtain 100 g of a bath salt.

TABLE 38

| | Weight (g) |
|---|---|
| Fragrance | 0.1 |
| Organic dye | 0.01 |
| Sodium Bicarbonate | 14.9 |
| Sodium Sulfate | 81.69 |
| Disodium ascorbate sulfate | 0.3 |

This bath salt is diluted about 3000-fold in use.

INDUSTRIAL APPLICABILITY

The enhancer of cellular response to cytokines of the present invention acts on skin cells to enhance their responsiveness to cytokines, thereby activating skin metabolism. As being able to penetrate through the skin, the ethanolamine derivatives of formula (I) and their salts can locally enhance the activity of cytokines. In addition, the ethanolamine derivatives and their salts are little toxic and therefore can enhance the activity of cytokines through systemic administration. Therefore, the ethanolamine derivatives of formula (I) and their salts are useful as cytokine activity enhancers.

We claim:

1. A cytokine formulation, comprising:
   a carrier;
   at least one of a cytokine and a cytokine production promoter; and
   at least one of a cytokine potentiator in an amount effective to treat a soft tissue wound, said cytokine potentiator including one of an ethanolamine derivative and a salt of said ethanolamine derivative, said ethanolamine derivative having the following general formula (I):

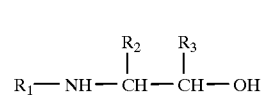

(I)

wherein:
   $R_1$ is selected from the group consisting of H, $CH_3$, and $CH_2CH_2OH$;
   $R_2$ is selected from the group consisting of H, $CH_3$, $CH_2CH_3$; and $R_3$ is selected from the group consisting of $CH_3$, $CH_2CH_3$ and $CH_2NH_2$.

2. A cytokine formulation, consisting essentially of:

at least one of a cytokine and a cytokine production promoter; and at least one of a cytokine potentiator in a combined amount effective to treat a soft tissue wound, said cytokine potentiator including one of an ethanolamine derivative and a salt of said ethanolamine derivative, said ethanolamine derivative having the following general formula (I):

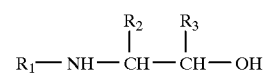

wherein:
$R_1$ is selected from the group consisting of H, $CH_3$, and $CH_2CH_2OH$;
$R_2$ is selected from the group consisting of H, $CH_3$ and $CH_2CH_3$; and
$R_3$ is selected from the group consisting of $CH_3$, $CH_2CH_3$ and $CH_2NH_2$.

* * * * *